(12) United States Patent
Sundaram

(10) Patent No.: US 11,903,911 B1
(45) Date of Patent: Feb. 20, 2024

(54) METHOD OF TREATING OBESITY BY REVERSAL OF NA/K-ATPASE INHIBITION

(71) Applicant: Marshall University Research Corporation, Huntington, WV (US)

(72) Inventor: Uma Sundaram, Huntington, WV (US)

(73) Assignee: MARSHALL UNIVERSITY RESEARCH CORPORATION, Huntington, WV (US)

(*) Notice: Subject to any disclaimer, the term of this patent is extended or adjusted under 35 U.S.C. 154(b) by 347 days.

(21) Appl. No.: 16/859,644

(22) Filed: Apr. 27, 2020

Related U.S. Application Data

(60) Provisional application No. 62/838,648, filed on Apr. 25, 2019.

(51) Int. Cl.
| | |
|---|---|
| *A61K 31/155* | (2006.01) |
| *A61P 3/04* | (2006.01) |
| *C12Q 1/25* | (2006.01) |
| *G01N 33/68* | (2006.01) |
| *G01N 33/50* | (2006.01) |

(52) U.S. Cl.
CPC .............. *A61K 31/155* (2013.01); *A61P 3/04* (2018.01); *C12Q 1/25* (2013.01); *G01N 33/5044* (2013.01); *G01N 33/6803* (2013.01); *G01N 2333/90* (2013.01)

(58) Field of Classification Search
CPC ...... A61K 31/155; A61K 38/16; A61K 38/43; A61K 38/46; A61K 38/00; A61K 38/10; A61P 3/04; A61P 3/06; G01N 2333/90; G01N 33/5044; G01N 33/6803; C12Q 1/25

See application file for complete search history.

(56) References Cited

PUBLICATIONS

Stricker-Krongrad et al., "Nitric Oxide Mediates Hyperphagia of Obese Zucker Rats: Relation to Specific Changes in Microstructure of Feeding Behavior", Life Sciences, vol. 58(1), pp. PL9-PL15 (Year: 1996).*

Zanella et al., "Treatment of Obesity Hypertension and Diabetes Syndrome", Hypertension, 2001, vol. 38[part 2], pp. 705-708 (Year: 2001).*

(Continued)

*Primary Examiner* — Savitha M Rao
(74) *Attorney, Agent, or Firm* — Stites & Harbison, PLLC; Terry L. Wright

(57) ABSTRACT

Methods of treating obesity include administering to a subject in need thereof an effective amount of a therapeutic agent capable of reversing an inhibition of a Na/K-ATPase in a small intestine of a subject, such as a basolateral membrane Na/K-ATPase. Administering the therapeutic agent can further decrease an amount of glucose transport and/or decrease an amount of salt absorption in the small intestine of the subject to thereby treat the obesity. Methods for screening for a compound useful for treating obesity include contacting a small intestine cell with an effective amount of a test compound, and detecting whether an activity level of a Na/K-ATPase in the small intestine cell is increased in the presence of the test compound. The test compound is then identified as a compound useful for the treatment of obesity if the activity level of the Na/K-ATPase is increased in the presence of the test compound.

6 Claims, 31 Drawing Sheets

(56) References Cited

PUBLICATIONS

Saydah, S., et al. (2014) Trends in cardiovascular disease risk factors by obesity level in adults in the United States, NHANES 1999-2010. Obesity (Silver Spring) 22, 1888-1895.

Centers for Disease Control and Prevention. (2017) National Diabetes Statistics Report, US Department of Health and Human Services, Atlanta, GA.

Lang, F., et al. (2006) (Patho)physiological significance of the serum and glucocorticoid-inducible kinase isoforms. Physiol. Rev. 86, 1151-1178.

He, P., et al. (2015) Restoration of Na+/H+ exchanger NHE3-containing macrocomplexes ameliorates diabetes associated fluid loss. J. Clin. Invest. 125, 3519-3531.

Leung, L., et al. (2014) Decreased basal chloride secretion and altered cystic fibrosis transmembrane conductance regulatory protein, Villin, GLUT5 protein expression in jejunum from leptin-deficient mice. Diabetes Metab. Syndr. Obes. 7, 321-330.

Donowitz, M., et al. (2005) NHERF family and NHE3 regulation. J. Physiol. 567, 3-11.

Sundaram, U., et al. (1991) pH regulation in ileum: Na(+)-H+ and Cl(−)-HCO3-exchange in isolated crypt and villus cells. Am. J. Physiol. 260, G440-G449.

Donowitz, M., et al. (2009) NHE3 regulatory complexes. J. Exp. Biol. 212, 1638-1646.

Kiela, P. R., et al. (2006) Apical NA+/H+ exchangers in the mammalian gastrointestinal tract. J. Physiol. Pharmacol. 67 (Suppl 7), 51-79.

Kato, A., et al. (2011)Regulation of electroneutral NaCl absorption by the small intestine. Annu. Rev. Physiol. 73, 261-281.

Malakooti, J., et al. (2011) Transcriptional regulation of the intestinal luminal Na+ and Cl2 transporters. Biochem. J. 435, 313-325.

Mount, D. B., et al. (2004) The SLC26 gene family of multifunctional anion exchangers. Pflugers Arch. 447, 710-721.

Schultheis, P. J., et al. (1998) Renal and intestinal absorptive defects in mice lacking the NHE3 Na+/H+ exchanger. Nat. Genet. 19, 282-285.

Alrefai, W. A., et al. (2003) Regulation of butyrate uptake in Caco-2 cells by phorbol 12-myristate 13-acetate. Am. J. Physiol. Gastrointest. Liver Physiol. 286, G197-G203.

Yun, C. C., et al. (2002) Glucocorticoid activation of Na(+)/H(+) exchanger isoform 3 revisited. The roles of SGK1 and NHERF2. J. Biol. Chem. 277, 7676-7683.

Amin, M. R., et al. (2007) Involvement of Sp1 and Sp3 in differential regulation of human NHE3 promoter activity by sodium butyrate and IFN-gamma/TNFalpha. Am. J. Physiol. Gastrointest. Liver Physiol. 293, G374-G382.

Lenzen, H., et al. (2012) Downregulation of the NHE3-binding PDZ-adaptor protein PDZK1 expression during cytokine-induced inflammation in interleukin-10-deficient mice. PLoS One 7, e40657.

Palaniappan, B., et al. (2018) Direct and specific inhibition of constitutive nitric oxide synthase uniquely regulates brush border membrane Na-absorptive pathways in intestinal epithelial cells. Nitric Oxide 79, 8-13.

Coon, S., et al. (2008) Constitutive nitric oxide differentially regulates Na-Hand Naglucose cotransport in intestinal epithelial cells. Am. J. Physiol. Gastrointest. Liver Physiol. 294, G1369-G1375.

Schweinfest, C.W., et al. (2006) slc26a3 (dra)-deficient mice display chloride-losing diarrhea, enhanced colonic proliferation, and distinct up-regulation of ion transporters in the colon. J. Biol. Chem. 281, 37962-37971.

Wang, Z., et al. (2005) Renal and intestinal transport defects in Slc26a6-null mice. Am. J. Physiol. Cell Physiol. 288, C957-C965.

Wright, E. M., et al. (2007) Active sugar transport in health and disease. J. Intern. Med. 261, 32-43.

Poulsen, S. B., et al. (2015) Sodium-glucose cotransport. Curr. Opin. Nephrol. Hypertens. 24, 463-469.

Bickel, C. A., et al. (2002) Dysregulation of renal salt and water transport proteins in diabetic Zucker rats. Kidney Int. 61, 2099-2110.

Kurtz, T. W., et al. (1989) The Zucker fatty rat as a genetic model of obesity and hypertension. Hypertension 13, 896-901.

Joost, H. G., et al. (2014) The genetic basis of obesity associated type 2 diabetes (diabesity) in polygenic mouse models. Mamm. Genome 25, 401-412.

Mao, X., et al. (2014) Islet insulin secretion, b-cell mass, and energy balance in a polygenic mouse model of type 2 diabetes with obesity. J. Inborn Errors Metab. Screen. 2, 1-6.

Sung, Y. Y., et al. (2005) Glucose intolerance in young TallyHo mice is induced by leptin-mediated inhibition of insulin secretion. Biochem. Biophys. Res. Commun. 338, 1779-1787.

Coon, S., et al. (2011) Reciprocal regulation of the primary sodium absorptive pathways in rat intestinal epithelial cells. Am. J. Physiol. Cell Physiol. 300, C496-C505.

Manoharan, P., et al. (2015) Chronic and selective inhibition of basolateral membrane Na-K-ATPase uniquely regulates brush border membrane Na absorption in intestinal epithelial cells. Am. J. Physiol. Cell Physiol. 308, C650-C656.

Sundaram, U., et al. (1999) Corticosteroids reverse the inhibition of Na-glucose cotransport in the chronically inflamed rabbit ileum. Am. J. Physiol. 276, G211-G218.

Sundaram, U., et al. (1997) Mechanism of inhibition of Na+-glucose cotransport in the chronically inflamed rabbit ileum. Am. J. Physiol. 273, G913-G919.

Sundaram, U., et al. (1997) Effect of chronic inflammation on electrolyte transport in rabbit ileal villus and crypt cells. Am. J. Physiol. 272, G732-G741.

Sundaram, U., et al. (1998) Unique mechanism of inhibition of Na+-amino acid cotransport during chronic ileal inflammation. Am. J. Physiol. 275, G483-G489.

Turner, J. R., et al. (2001) NHE3-dependent cytoplasmic alkalinization is triggered by Na(+)-glucose cotransport in intestinal epithelia. Am. J. Physiol. Cell Physiol. 281, C1533-C1541.

Coon, S., et al. (2003) Unique regulation of anion/HCO3-exchangers by constitutive nitric oxide in rabbit small intestine. Am. J. Physiol. Gastrointest. Liver Physiol. 285, G1084-G1090.

Manokas, T., et al. (2000) Effect of chronic inflammation on ileal short-chain fatty acid/bicarbonate exchange. Am. J. Physiol. Gastrointest. Liver Physiol. 278, G585-G590.

Manoharan, P., et al. (2013) Prostaglandins, not the leukotrienes, regulate Cl(−)/HCO(3)(−) exchange (DRA, SLC26A3) in villus cells in the chronically inflamed rabbit ileum. Biochim. Biophys. Acta 1828, 179-186.

Hodges, K., et al. (2006) Rapid activation of Na+/H+ exchange by EPEC is PKC mediated. Am. J. Physiol. Gastrointest. Liver Physiol. 291, G959-G968.

Gorboulev, V., et al. (2012) Na(+)-D-glucose cotransporter SGLT1 is pivotal for intestinal glucose absorption and glucose-dependent incretin secretion. Diabetes 61, 187-196.

Sundaram, U., et al. (1997) Mechanism of inhibition of Na+-glucose cotransport in the chronically inflamed rabbit ileum. American Journal of Physiology-Gastrointestinal and Liver Physiology 273(4):G913-G919.

Sundaram, U., et al. (1998) Unique mechanism of inhibition of Na+-amino acid cotransport during chronic ileal inflammation. American Journal of Physiology-Gastrointestinal and Liver Physiology 275(3):G483-G489.

Zhang, T., et al. Long-term Impact of Temporal Sequence from Childhood Obesity to Hyperinsulinemia on Adult Metabolic Syndrome and Diabetes: The Bogalusa Heart Study. Scientific reports 7, 43422, doi: 10.1038/srep43422 (2017).

Feng, W., et al. Novel Paradigms of Salt and Hypertension. Journal of the American Society of Nephrology : JASN, doi:10.1681/asn. 2016080927 (2017).

Coon, S., et al. (2005) Na-glucose and Na-neutral amino acid cotransport are uniquely regulated by constitutive nitric oxide in rabbit small intestinal villus cells. American Journal of Physiology-Gastrointestinal and Liver Physiology 289 (6):G1030-G1035.

(56) References Cited

PUBLICATIONS

Shen, S.W., et al. Comparison of impedance to insulin-mediated glucose uptake in normal subjects and in subjects with latent diabetes. The Journal of clinical investigation 49, 2151-2160, doi:10.1172/jci106433 (1970).

Sharabi, Y. Management of the unholy trinity diabetes-obesity-hypertension (diabesotension). Diabetes/metabolism research and reviews, doi:10.1002/dmrr.2371 (2012).

Palaniappan, B., et al. (2019). Inhibition of intestinal villus cell Na/K-ATPase mediates altered glucose and NaCl absorption in obesity-associated diabetes and hypertension. The FASEB Journal, 33(8), 9323-9333.

Arthur, S., et al. (2014) Regulation of sodium glucose co-transporter SGLT1 through altered glycosylation in the intestinal epithelial cells. Biochimica et biophysica acta 1838(5):1208-1214.

* cited by examiner

METHOD OF TREATING OBESITY BY REVERSAL OF NA/K-ATPASE INHIBITION

RELATED APPLICATIONS

This application claims priority from U.S. Provisional Application Ser. No. 62/838,648, filed Apr. 25, 2019, the entire disclosure of which is incorporated herein by this reference.

GOVERNMENT INTEREST

This invention was made with government support under grant numbers DK-67420 and DK-108054 awarded by the National Institutes of Health. The government has certain rights in the invention.

TECHNICAL FIELD

The presently-disclosed subject matter generally relates to methods of treating and screening for compounds for treatment of obesity, diabetes, and/or hypertension. In particular, certain embodiments of the presently-disclosed subject matter relate to methods for treating and screening for compounds for treatment of obesity that make use of therapeutic agents capable of reversing an inhibition of the Na/K-ATPase in obese subjects.

BACKGROUND

The obesity epidemic in the United States affects more than one-third (34.9% or 78.6 million) of adults. In obesity, the prevalence of diabetes was 18.5% and hypertension 35.7%. The most recent available data from the Centers for Disease Control and Prevention indicate that the prevalence of diabetes in this country is 30.3 million or 9.4% of the population, and this almost triples in Americans over the age of 65. Altered glucose homeostasis is central to the pathophysiology of diabetes. Along with glucose metabolism, insulin activity, and gluconeogenesis, intestinal assimilation of glucose is important in maintaining glucose homeostasis. Further, approximately 75 million American adults or approximately 1 out of every 3 adult Americans has high blood pressure. This prevalence more than doubles in Americans over the age of 65 (64.0% in men and 69.3% in women). Altered sodium (Na) homeostasis is central to the pathophysiology of hypertension. Along with aldosterone and renal handling, intestinal absorption of Na is important for maintaining Na homeostasis. At a larger level, in the Western hemisphere, 15% of the population suffers from obesity, diabetes, and hypertension with resultant health care disparities.

In obesity, deregulation of glucose homeostasis not only results in diabetes but also obesity because hyperglycemia promotes obesity by excessive insulin release and subsequent fat deposition. Similarly, altered NaCl homeostasis directly results in hypertension. However, how intestinal assimilation of NaCl and glucose may be affected in obesity to cause this ubiquitous triad is unclear.

The primary function of the mammalian small intestine is absorption of nutrients, electrolytes, and water. The daily absorption of approximately 7.5 L of water is mediated by the absorption of Na and Cl. Coupled NaCl absorption is mediated by the dual operation of Na—H and Cl—$HCO_3$ exchanges located in the brush border membrane (BBM) of absorptive villus but not secretory crypt cells. Intracellular pH mediates this functional coupling in the villus-cell BBM. The crypt cell only has a Cl—$HCO_3$ exchange on the BBM; thus, it is incapable of coupled NaCl absorption. Na—H exchange in villus-cell BBM is mediated by the solute carrier (SLC)-9A3 [Na—H exchange 3 (NHE3)] of the SLC9 gene family, whereas Cl—$HCO_3$ exchange is mediated by the down-regulated in adenoma (DRA; SLC26A3) and putative anion transporter 1 (PAT1; SLC26A6) of the SLC26 gene family in the mammalian intestine. The phenotype of the NHE3$^{-/-}$ mice, specifically diarrhea, low blood pressure, and mild metabolic acidosis, illustrates the significance of NHE3 for Na and resultant water absorption in the small intestine. A variety of agents have been shown to regulate NHE3, including but not limited to NO, Phorbol 12-myristate 13-acetate, glucocorticoids, butyrate, IFN-γ, TNF-α, and IL-1β.

The significance of DRA in NaCl-mediated water absorption is illustrated by the phenotype of DRA knockout mice, namely watery stool with high chloride concentration and metabolic alkalosis, which is similar to congenital chloride diarrhea in humans. In contrast, although PAT1 knockout mice showed diminished Cl—$HCO_3$ exchange activity, it did not result in diarrhea, implying that, unlike DRA, PAT1 may not be directly coupled to water absorption. Coupled NaCl absorption has been shown to be regulated by norepinephrine, acetylcholine, vasoactive intestinal peptide, angiotensin II, neuropeptide Y, serotonin, substance P, somatostatin, encephalin, peptide YY, prostaglandin E2, IFN-γ, glucocorticoid, guanylin, and uroguanylin. Yet whether obesity may affect NHE3, DRA, or PAT and thus coupled NaCl absorption to cause hypertension is also unknown.

Na-glucose cotransport 1 (SGLT1, SLC5A1) is the most abundant Na-dependent nutrient-absorptive process in the mammalian small intestine. It is also found in the BBM of absorptive villus but not crypt cells. SGLT1 is a secondary active transport process requiring a favorable transcellular Na gradient, which is provided by the Na/K-ATPase located in the basolateral membrane (BLM) of villus cells. Thus, at the cellular level, regulation of SGLT1 may be at the BBM cotransporter level and at the Na-extruding capacity of the cell level. SGLT1 is not only important for sodium absorption but also for glucose absorption, which is the most abundant nutrient in the diet. Preserved SGLT1 is the basis for oral rehydration, which is the most important treatment for the number one cause of infant mortality in developing countries, diarrhea, in which coupled NaCl absorption is diminished and SGLT1 is preserved. Regulation of SGLT1 by cAMP, PKA and PKC, insulin, leptin, glucagon-like peptide 2, MAPKs, NF-κB, STAT3, and PI3K/Akt has been reported.

Apart from numerous agents that have been shown to affect NHE3 and SGLT1, there is emerging evidence that, in fact, NHE3 and SGLT1 regulate one another. When NHE3 was silenced in intestinal epithelial cell (IEC-18) monolayers with NHE3 small interfering RNA (siRNA), the cells demonstrated decreased NHE3 activity, mRNA, and protein. However, in NHE3-silenced cells, SGLT1 activity, mRNA, and protein in the BBM were significantly increased. Thus, inhibition of NHE3 expression compensatorily increased the expression and function of SGLT1 in the BBM of intestinal epithelial cells. Further, silencing SGLT1 in IEC-18 cells diminished SGLT1 activity, mRNA, and protein levels. However, in these cells, NHE3 activity, mRNA, and protein levels were increased. Therefore, the inhibition of SGLT1 expression stimulated the transcription and function of NHE3 and vice versa in the BBM of intestinal epithelial cells. Nevertheless, how these distinct transport processes may be coordinately regulated to disrupt glucose and NaCl homeostasis in obesity resulting in diabetes and hypertension is not known as well.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

The presently-disclosed subject matter includes methods of treating and screening for compounds for treatment of obesity, diabetes, and/or hypertension. In particular, certain embodiments of the presently-disclosed subject matter include methods for treating and screening for compounds for treatment of obesity that make use of therapeutic agents capable of reversing an inhibition of the Na/K-ATPase in obese subjects. In some embodiments, a method of treating obesity is provided that comprises administering to a subject in need thereof an effective amount of a therapeutic agent capable of reversing an inhibition of a Na/K-ATPase in a small intestine of a subject. In some embodiments, the subjects administered the therapeutic agent are obese, have diabetes, and/or have hypertension.

In some embodiments, the Na/K-ATPase undergoing a reversal of inhibition is a basolateral membrane Na/K-ATPase. In some embodiments, administering the therapeutic agent decreases an amount of glucose transport and/or decreases an amount of sodium chloride (NaCl) absorption in the small intestine of the subject. For instance, in some embodiments, administering the therapeutic agent decreases glucose transport by a Na-glucose cotransport 1 (SGLT1) protein in the small intestine. In some embodiments, administering the therapeutic agent decreases an activity or expression level of a down-regulated in adenoma (DRA) protein and/or putative anion transporter 1 (PAT1) protein in the small intestine.

For administration of the therapeutic agent, in some embodiments, administering the therapeutic agent comprises contacting a villus cell in the small intestine of the subject with the therapeutic agent. In some embodiments, the therapeutic agent is selected from the group consisting of nitric oxide synthase (NOS) inhibitors, glucocorticoids, cyclooxygenase inhibitors, lipoxygenase inhibitors, prostaglandins, leukotrienes, interleukins, tumor necrosis factor alpha, antioxidants, angiotensin II, insulin-like growth factor-I, serum- and glucocorticoid-inducible kinase 1 (SGK1), SGK1 stimulators, vitamin D, β-Catenin, pNaKtide, 70 kDa inhibitor protein of Na(+)/K(+) ATPase, curcumin, ceramide, nitroprusside, and phospholemman. In some embodiments, the therapeutic agent is $N^G$-nitro-L-arginine methyl ester (L-NAME).

Further provided, in some embodiments of the presently-disclosed subject matter, are methods for screening for a compound useful for treating obesity. In some embodiments, such a screening method includes contacting a small intestine cell with an effective amount of a test compound, and then detecting whether an activity level of a Na/K-ATPase in the small intestine cell is increased in the presence of the test compound. In some embodiments, the test compound is then identified as a compound useful for the treatment of obesity if the activity level of the Na/K-ATPase is increased in the presence of the test compound.

With respect to the detection of the activity level of the Na/K-ATPase in the accordance with the screening methods, in some embodiments, the Na/K-ATPase is a basolateral membrane Na/K-ATPase. In some embodiments, detecting whether an activity level of a Na/K-ATPase in the small intestine cell is increased comprises detecting, prior to administration of the test compound, whether the activity level of the Na/K-ATPase is reduced. In this regard, in some embodiments, detecting whether an activity level of a Na/K-ATPase in the small intestine cell is increased further comprises detecting, subsequent to administration of the test compound, whether the reduced activity level of the Na/K-ATPase is reversed.

In some embodiments of the screening methods described herein, the screening methods further include a step of detecting an amount of glucose transport and/or an amount of sodium chloride (NaCl) absorption in the small intestine cell of the subject. In some embodiments, the test compound is identified as a compound useful for the treatment of obesity if, subsequent to contacting the cell with the test compound, the amount of glucose transport and/or salt (e.g., NaCl) absorption is decreased in the cell. In some embodiments, detecting the amount of glucose transport comprises detecting the amount of glucose transport by a Na-glucose cotransport 1 (SGLT1) protein in the small intestine.

In further embodiments of the screening methods, the screening methods can also include a step of detecting an activity or expression level of a down-regulated in adenoma (DRA) protein and/or putative anion transporter 1 (PAT1) protein in the small intestine cell of the subject. In such embodiments, the test compound can then be identified as a compound useful for the treatment of obesity if, subsequent to contacting the cell with the test compound, the DRA or PAT1 protein activity or expression level is decreased in the cell.

Further features and advantages of the present invention will become evident to those of ordinary skill in the art after a study of the description, figures, and non-limiting examples in this document.

DESCRIPTION OF EXEMPLARY EMBODIMENTS

Figure 1A:
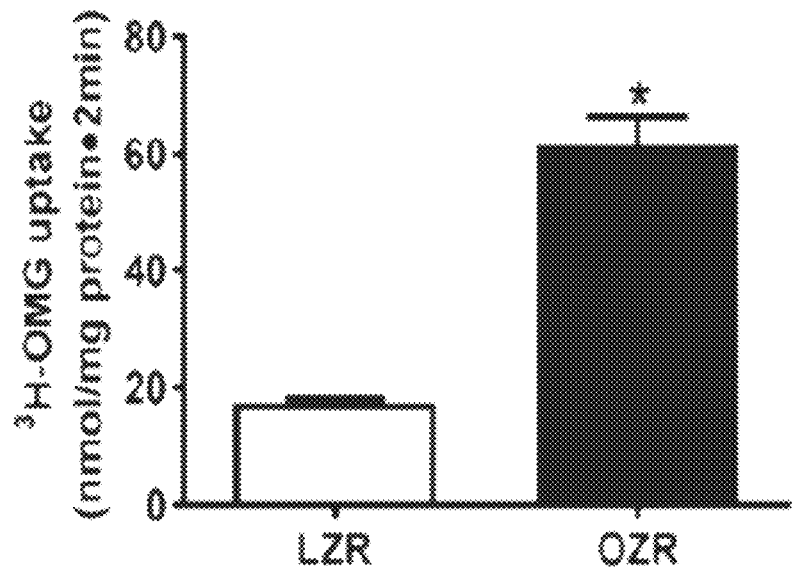
FIGS. 1A-1D include graphs showing the effect of obesity on Na-dependent glucose uptake in intestinal ileal villus cells, including graphs showing that SGLT1 was significantly stimulated in intact ileal villus cells (FIG. 1A) and BBMV preparations (FIG. 1B) from OZRs compared with LZRs, and graphs showing that those observations were consistent in the BBMV preparations in TOM (FIG. 1C) and obese humans (FIG. 1D), and where, for all experiments, n represents different studies performed with intestinal cells isolated from a different host each time; n=4. *P<0.01.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it is understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments±1%, in some embodiments ±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

In obesity, diabetes and hypertension inevitably co-exist, resulting from the deregulation of glucose and sodium chloride (NaCl) homeostasis, respectively, and, in turn, cause innumerable health disparities. In the mammalian small intestine, glucose is primarily absorbed by Na-glucose co-transport (SGLT1) and coupled NaCl by the dual operation of Na:H (NHE3) and Cl:$HCO_3$ (Down Regulated in Adenoma (DRA) or Putative Anion Transporter 1 (PAT1)) exchange on the brush border membrane (BBM) of villus cells. The favorable trans cellular Na-gradient for SGLT1 and NHE3 is provided by Na/K-ATPase on the basolateral membrane (BLM). However, how these multiple distinct transport processes may be coordinately regulated to disrupt glucose and NaCl homeostasis in obesity associated diabetes and hypertension was previously undetermined. It has now been surprisingly discovered, however, that the broad regulation by Na/K-ATPase of glucose and NaCl absorption in obesity in multiple species can cause associated diabetes and hypertension. In particular, it has been observed that in obese rats, mice, and humans, villus cell BBM NHE3 is unaffected while SGLT1 is stimulated and DRA/PAT1 is stimulated to maintain electro neutrality. Thus, in obesity, it has been found that NaCl absorption is increased as a result of a novel coupling of stimulated SGLT1 with DRA/PAT1 and that glucose absorption is enhanced from increased SGLT1. Further, increased SGLT1 is not secondary to enhanced Na/K-ATPase activity, which is diminished during obesity. Without wishing to be bound by any particular theory or mechanism, it was therefore believed that this unique and primary alteration of BLM Na/K-ATPase in obesity stimulates BBM SGLT1 and subsequently DRA/PAT1 as a cellular adaptive mechanism. These results, in three species, demonstrated that in obesity intestinal villus cell BLM Na/K-ATPase inhibition compensatorily stimulated BBM SGLT1 and DRA/PAT1 resulting in enhanced glucose and NaCl absorption. Therefore, the presently-disclosed subject matter, is based, at least in part, on the discovery of a pathophysiologic basis for the deregulation of glucose and NaCl homeostasis of diabetes and hypertension, respectively, in obesity.

The presently-disclosed subject matter thus includes methods of treating and screening for compounds for treatment of obesity, diabetes, and/or hypertension. In particular, in some embodiments of the presently-disclosed subject matter, methods for treating obesity are provided that make use of compounds or therapeutic agents capable of reversing an inhibition of the Na/K-ATPase in obese subjects. In some embodiments, a method of treating obesity is provided that comprises administering to a subject in need thereof an effective amount of a therapeutic agent capable of reversing an inhibition of a Na/K-ATPase.

The term "obesity," as used herein, refers to conditions in which excess body fat has accumulated to the extent that it may have a negative effect on health, which can, in turn, lead to reduced life expectancy and/or increased health problems. In certain instances, a subject can be considered obese when their body mass index (BMI), a measurement obtained by dividing a subject's weight by the square of the person's height, is greater than 20 kg/m$^2$, 21 kg/m$^2$, 22 kg/m$^2$, 23 kg/m$^2$, 24 kg/m$^2$, 25 kg/m$^2$, 26 kg/m$^2$, 27 kg/m$^2$, 28 kg/m$^2$, 29 kg/m$^2$, or 30 kg/m$^2$. Obesity can also coincide with conditions such as, but not limited to, hyperinsulinemia, insulin resistance, diabetes, hypertension, and dyslipidemia. Obesity can further be a risk factor for cardiovascular disease. In some instances, obesity can also be characterized by one or more of fasting glucose levels of at least 100 mg/dl, plasma triglyceride levels of at least 150 mg/dl, HDL cholesterol below 40 mg/dl in men and below 50 mg/dl in women, blood pressure of at least 130/85 mm Hg, and abdominal waist circumference of greater than 40 inches for men and greater than 35 inches for women. Accordingly, in some embodiments, reference to the treatment of obesity, as used herein, includes, but is not limited to, the treatment of obesity, diabetes, and/or hypertension.

In this regard, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes: palliative treatment, or treatment designed for the relief of symptoms rather than the curing of the disease, pathological condition, or disorder; preventative treatment, or treatment directed to minimizing or partially or completely inhibiting the development of the associated disease, pathological condition, or disorder; and supportive treatment, or treatment employed to supplement another therapy directed toward the improvement of the associated disease, pathological condition, or disorder.

The treatment of obesity can be measured and quantified in several different ways and by taking into account several characteristics of obesity. In some embodiments, treatment of obesity can be measured and quantified by, among other things, an increase in the amount of glucose transport and/or an increase in the amount of salt (e.g., NaCl) absorption, such as what occurs in the small intestine of a subject. Such measurements and quantifications can be performed by any number of methods known to those skilled in the art. In some embodiments, increases and/or decreases described herein can be in reference to a control subject suffering from obesity and that has not been treated in accordance with the presently-disclosed subject matter.

With further respect to the treatment of obesity as described herein, in some embodiments, administering the therapeutic agent comprises contacting a small intestine of a subject with the therapeutic agent as it has now been determined that Na/K-ATPase inhibition in the small intestine of a subject results in enhanced glucose and NaCl absorption. In this regard, in some embodiments, contacting the small intestine with or otherwise administering the therapeutic agent decreases an amount of glucose transport and/or decreases an amount of salt (e.g., NaCl) absorption in the small intestine of the subject. For example, in some embodiments, administering the therapeutic agent decreases glucose transport by the Na-glucose cotransport 1 (SGLT1) protein in the small intestine cells of a subject. In some embodiments, administering the therapeutic agent decreases an activity or expression level of a down-regulated in adenoma (DRA) protein and/or a putative anion transporter 1 (PAT1) protein in a cell of the small intestine. In some embodiments, contacting the small intestine with the therapeutic agent comprises contacting a villus cell with the therapeutic agent.

For administration of a therapeutic composition as disclosed herein (e.g., a therapeutic agent that reverses the inhibition of the Na/K-ATPase), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered intravenously or orally to treat a disease or disorder.

Regardless of the route of administration, the therapeutic agents used in accordance with the presently-disclosed subject matter are typically administered in an amount effective to achieve the desired response. As such, the term "effective amount" is used herein to refer to an amount of the therapeutic composition sufficient to produce a measurable biological response (e.g., a decrease in inhibition of the Na/K-ATPase). Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

With respect to the particular therapeutic agents capable of being utilized in a accordance with the presently-described therapeutic methods, a number of therapeutic agents can be utilized to alter the activity of a Na/K-ATPase, such as those found in the small intestine cells of a subject. In some embodiments, the therapeutic agent used in accordance with the presently-disclosed subject matter to reverse an inhibition of a Na/K-ATPase is selected from the group consisting of nitric oxide synthase (NOS) inhibitors, glucocorticoids, cyclooxygenase inhibitors, lipoxygenase inhibitors, prostaglandins, leukotrienes, interleukins, tumor necrosis factor alpha, antioxidants, angiotensin II, insulin-like growth factor-I, serum- and glucocorticoid-inducible kinase 1 (SGK1), SGK1 stimulators, vitamin D, β-Catenin, pNaKtide (see, e.g., U.S. Patent Application Publication No. 2014/0187484), 70 kDa inhibitor protein of Na(+)/K(+) ATPase, curcumin, ceramide, nitroprusside, and phospholemman. In some embodiments, the therapeutic agent is $N^G$-nitro-L-arginine methyl ester (L-NAME). Each of the foregoing agents meditate their therapeutic effect via one of three intracellular messengers—calcium (lipoxygenase inhibitors, leukotrienes, interleukins); cyclic AMP (cyclooxygenase inhibitors, prostaglandins) or cyclic GMP (nitric oxide synthase (NOS) inhibitors); or PIP3/diacylglycerol (insulin-like growth factor-I, SGK1)—which subsequently work via their specific dependent protein kinases to inhibit the α1 subunit of the Na/K-ATPase. Depending on the protein kinase affected by the given agent (above in parentheses), the mechanism by which the α1 subunit inhibition may be reduced will be secondary to its synthesis, phosphorylation, its trafficking from the cytosol to the basolateral membrane, or a combination of the foregoing. Given the particular disease condition and mechanism involved, however, an agent can then be readily selected that will mediate the reversal of the inhibition of the Na/K-ATPase by its effect on a particular pathway, such that the specific treatment being selected is based on the specific agent and pathway.

Further provided, in some embodiments of the presently-disclosed subject matter, are methods for screening for a compound useful for treating obesity. In some embodiments, such a screening method includes contacting a small intestine cell with an effective amount of a test compound, and then detecting whether an activity level of a Na/K-ATPase in the small intestine cell is increased in the presence of the test compound. In some embodiments, the test compound is then identified as a compound useful for the treatment of obesity if the activity level of the Na/K-ATPase is increased in the presence of the test compound. In this regard, in some embodiments, the term test compound can be used interchangeably herein with the term "therapeutic agents" to refer to those agents capable of reversing an inhibition of a Na/K-ATPase. Furthermore, the term "test compound" is not intended to be limited to small molecules but is inclusive of biological and other agents capable of reversing an inhibition of a Na/K-ATPase.

In some embodiments of the screening methods described herein, the Na/K-ATPase is a basolateral membrane Na/K-ATPase. In some embodiments, detecting whether an activity level of a Na/K-ATPase in the small intestine cell is increased comprises detecting, prior to administration of the test compound, whether the activity level of the Na/K-ATPase is reduced. In this regard, in some embodiments, detecting whether an activity level of a Na/K-ATPase in the small intestine cell is increased further comprises detecting, subsequent to administration of the test compound, whether the reduced activity level of the Na/K-ATPase is reversed.

In some embodiments of the screening methods described herein, the screening methods further include a step of detecting an amount of glucose transport and/or an amount of sodium chloride (NaCl) absorption in the small intestine cell of the subject. In some embodiments, the test compound is identified as a compound useful for the treatment of obesity if, subsequent to contacting the cell with the test compound, the amount of glucose transport and/or salt (NaCl) absorption is decreased in the cell. In some embodiments, detecting the amount of glucose transport comprises detecting the amount of glucose transport by a Na-glucose cotransport 1 (SGLT1) protein in the small intestine.

In further embodiments of the screening methods, the screening methods can also include a step of detecting an activity or expression level of a down-regulated in adenoma (DRA) protein and/or putative anion transporter 1 (PAT1) protein in the small intestine cell of the subject. In such embodiments, the test compound can then be identified as a compound useful for the treatment of obesity if, subsequent to contacting the cell with the test compound, the DRA or PAT1 protein activity or expression level is decreased in the cell.

Various methods known to those of ordinary skill in the art can be used to determine Na/K-ATPase as well as other protein (e.g., SGLT1, DRA, PAT1) expression level or activity in a cell of a subject, such as to determine whether an inhibition of such activity has been reversed. For example, in some embodiments, a reversal in the inhibition of Na/K-ATPase activity can be measured by determining an amount of inorganic phosphate released from cellular homogenates obtained from a sample from a subject. See, e.g., Forbush, et al., *Analytical Biochemistry*, 128, 159-163, which is incorporated herein by reference. As another example, in some embodiments, glucose transport measurement or sodium transport measurements can be made by incubating cells in the presence of appropriate glucose or sodium isotopes followed by a determination of the radioactivity of the cells by a scintillation counter. See, e.g., Palaniappan, et al., *Nitric Oxide*, 79, 8-13; see also Turner, et al., Am. J. Physiol. Cell Physiol., 281, C1533-C1541; see also Hodges, et al., Am. J. Physiol. Gastrointest. Liver Physiol. 291, G959-G968, each of which are also incorporated herein by reference.

Of course, determination of protein expression levels can also be made by any number of methods known to those skilled in the art including, but not limited to, of ELISA, Luminex, FACs, Western blot, dot blot, immunoprecipitation, immunohistochemistry, immunocytochemistry, immunofluorescence, immunodetection methods, optical spectroscopy, radioimmunoassay, mass spectrometry, HPLC, qPCR, RT-qPCR, multiplex qPCR, SAGE, RNA-seq, microarray analysis, FISH, MassARRAY technique, and combinations thereof.

With respect to the reversal of the observed inhibition of Na/K-ATPase activity as well as the decrease in glucose transport and salt absorption, the terms "reversal" or "inhibition" or "decrease" or "reduction" do not necessarily refer to the ability to completely reverse or completely inactivate all target biological activity in all cases. Rather, the skilled artisan will understand that the term "inhibiting" as well as the term "reversal" or "reduce" refers to decreasing biological activity or inactivity of a target. Such decreases in biological activity or inactivity can be determined relative to a control, wherein the control can be representative of an environment in which a therapeutic agent or candidate compound is not administered. For example, in some embodiments, a decrease in activity or inactivity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

With still further regard to the various methods described herein, although certain embodiments of the methods disclosed herein only call for a qualitative assessment, other embodiments of the methods call for a quantitative assessment. Such quantitative assessments can be made, for example, using known methods, as will be understood by those skilled in the art.

The skilled artisan will also understand that measuring a reversal of inhibition of a Na/K-ATPase or change in other activity or expression level is a statistical analysis. For example, a reduction in inhibition can be compared to control level of inhibition (e.g., a level of inhibition observed in an obese subject), and an amount of Na/K-ATPase activity of less than or equal to the control level can be indicative of a reduction in the inhibition, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1—Inhibition of Intestinal Villus Cell Na/K-ATPase Mediates Altered Glucose and NaCl Absorption in Obesity-Associated Diabetes and Hypertension Materials and Methods Animal models. Zucker rats [Strain 185 (obese, OZR) and 186 (lean, LZR); males, 18 wks] were obtained from Charles River Laboratories (Wilmington, MA, USA). TallyHo/JngJ mice (TOM) (males, 21 wks) and C57BL/6 mice (males, 21 wks) were obtained from The Jackson Laboratory (Bar Harbor, ME, USA). The animals were maintained in a 12-h light/dark cycle with free access to food and water. Animals were handled and euthanized according to Marshall University's Institutional Animal Care and Use Committee's ethics and regulation guidelines as accredited by the Association for Assessment and Accreditation of Laboratory Animal Care.

Cell lines and RNA interference. IEC-18 cells, a well-authenticated model of rat ileal epithelial cells, were obtained from American Type Culture Collection (ATCC; CRL-1589). Cells were used only between passages 5 and 25 and grown in high-glucose DMEM supplemented with 0.2 U/ml of insulin, 0.5 mM β-hydroxybutyrate, and 10% fetal calf serum and incubated at 37° C. with 10% C02 in a humidified atmosphere. Transient transfections to inhibit Na/K-ATPase-α1 expression were performed as previously described. Briefly, silencer predesigned negative control (scrambled siRNA; 4635; Thermo Fisher Scientific, Waltham, MA, USA) and Na/K-ATPase siRNAs (4390771 and s127474) were used for siRNA transfections. Seven days-post-transfected monolayers in 24-well plates were used for all the transport studies.

Human specimen. After informed consent, small-intestinal ileal biopsies were obtained from obese (body mass index>35) individuals without other intestinal pathology. All the intestinal specimen from humans were obtained according to the Marshall University Institutional Review Board's regulated and approved protocol (964144-1).

Na/K-ATPase measurement. Na/K-ATPase activity was measured as inorganic phosphate released from cellular homogenates using a method previously described. Enzyme-specific activity was expressed as nanomoles of Pi liberated per milligram protein per minute.

Uptake studies in intact ileal villus cells and BBM vesicles. Ileal villus cells were isolated from the intestines of the experimental animals by a calcium chelation technique. Ileal villus BBM vesicles (BBMVs) from animal and human intestines were prepared by $Mg^{++}$ precipitation and differential centrifugation. Na-glucose cotransport uptake studies in intact ileal villus cells (Zucker rats alone) and BBMVs (Zucker rats, TallyHo, and human ileal villus cells) were performed by the rapid-filtration technique as previously described. In brief, for intact ileal villus cell uptake, 10 µl of ileal villus cells were suspended in Na-free buffer. The ileal villus cells were then incubated in 90 µl of reaction medium that contained Na-buffer, 10 µCi of $^3H$—O-methyl glucose (OMG), and 100 µM OMG in the presence or absence of 1 mM phlorizin. At 2 min, uptake was arrested by mixing with ice-cold stop solution (Na-free buffer) containing 25 mM D-glucose. The mixture was filtered on 0.65-mm Millipore (HAWP) filters and washed twice with 5 ml ice-cold stop solution. Filters were dissolved in 5 ml scintillation fluid (Ecoscint; National Diagnostics, Atlanta, GA, USA), and radioactivity was determined in a Beckman 6500 Beta Scintillation Counter (Beckman Coulter, Brea, CA, USA).

For BBMV uptakes, the uptakes were performed as for cells but were arrested at 90 s, and reaction mixture was filtered on 0.45-µm Millipore (HAWP) filters. To determine the kinetic parameters of BBM Na-glucose cotransport, BBMV uptakes were performed with increasing concentrations of extravesicular OMG (50 µM to 50 mM) at a constant time point of 30 s. The uptake data derived from these experiments were analyzed with GraphPad Prism 7 (GraphPad Software, La Jolla, CA, USA) for Michaelis-Menten kinetics using a nonlinear regression data analysis to derive kinetic parameters.

Na—H exchange uptake was measured in BBMV by rapid filtration technique as previously described. Briefly, 5 µl of BBMV was suspended in vesicle medium and incubated in 95 µl of reaction medium and with or without 1 mM amiloride. At 60 s, uptake was arrested by mixing with ice-cold stop solution and processed as described for Na-glucose cotransport uptake studies.

$Cl$—$HCO_3$ exchange uptake was measured in BBMV by rapid filtration technique as previously described. BBMV was suspended in vesicle medium and either 50 mM $KHCO_3$ (vesicle gassed with 5% $CO_2$ and 95% $N_2$) or 50 mM potassium gluconate (vesicle gassed with 100% $N_2$). The reaction was started by adding 5 µl of vesicle to 95 µl reaction mixture with or without 1 mM 4,4-diisothiocyanatostilbene-2,2-disulfonic acid disodium salt (DIDS), a potent anion exchange inhibitor. The uptake was stopped at 60 s with ice-cold stop solution and processed as described above.

Uptake studies in IEC-18 cells. Na-glucose cotransport studies were performed using $^3H$—OMG as previously described. Briefly, cells were washed and incubated with Na-free buffer, as described above for BBMV studies, for 10 min. Uptake was initiated by incubating the cells for 2 min in reaction medium in the presence or absence of 1 mM phlorizin and 10 mM D-glucose as described above for BBMV studies. The reaction was stopped, and the cells were washed twice with ice-cold Na-free buffer containing 25 mM D-glucose. The cells were then incubated with 1 N NaOH for 20 min at 70° C. to digest the cells before the addition of 4 ml of scintillation fluid (Ecoscint; National Diagnostics). Radioactivity was determined in a Beckman 6500 Beta Scintillation Counter. SGLT1-specific uptake was calculated by subtracting uptake with and without phlorizin.

Na—H exchange was initiated in IEC-18 cells with Na-free buffer containing 10 µCi of $^{22}Na$ and 1 mM NaCl in the presence or absence of 50 µM EIPA, as previously described. Briefly, the cells were preincubated for 10 min in acid load and washed with wash buffer, following by addition of the reaction mixtures. $^{22}Na$ uptake reaction was arrested at 2 min, and the cells were washed twice with ice-cold PBS and processed as described above.

$Cl$—$HCO_3$ exchange was performed using $^{36}Cl$ as the substrate. Briefly, cells were incubated for 10 min in gluconate buffer containing 115 mM Na gluconate, 5 mM K-gluconate, 25 mM $NaHCO_3$, and 20 mM Tris-HEPES (pH 7.5) at room temperature. Uptake was initiated by the addition of the reaction medium containing 115 mM Na gluconate, 5 mM K-gluconate, 4 mM $NaHCO_3$, 20 mM Tris-MES (pH 5.5), 5 mM NMG, and 2.5 mM HCl with $^{36}HCl$ in the presence or absence of 1 mM DIDS. $^{36}Cl$ uptake was arrested at 2 min, and the cells were washed with ice cold gluconate buffer and processed as previously described.

Western blot study. All the Western blot experiments were performed with standard protocols and techniques. Solubilized BBM proteins from rat, mouse, human, and IEC-18 cells were separated (custom-made 8% polyacrylamide gel) and transferred to a BioTrace PVDF membrane. For immunoreactive protein determination, membranes were probed with protein-specific and species-reactive antibodies. For mice, anti-SGLT1 antibody raised in rabbit (ab14686; Abcam, Cambridge, MA, USA) was used. For rat and human samples, anti-SGLT1 antibody raised in chicken (custom antibody services; Thermo Fisher Scientific) was used. For NHE3, anti-NHE3 antibody raised in chicken (custom antibody services; Thermo Fisher Scientific) was used. Anti-DRA antibody raised in goat (sc-34939; Santa Cruz Biotechnology, Dallas, TX, USA) and anti-PAT1 antibody raised in goat (sc-26728; Santa Cruz Biotechnology) were also used for this study. Horseradish peroxidase-coupled specific secondary antibodies were used to detect the proteins before chemiluminescence with ECL Detection Reagent (GE Healthcare, Waukesha, WI, USA). The protein densities of the specific proteins were quantitated with a densitometric scanner FluorChemTMinstrument (ProteinSimple, San Jose, CA, USA).

Immunofluorescence study. Immunofluorescence for SGLT1, NHE3, DRA, and PAT1 were performed as previously described. Briefly, a portion of ileum was embedded in Cryo-OCT compound (Leica Microsystems, Buffalo Grove, IL, USA) and frozen in liquid nitrogen. Tissue sections (5 µm) that were made with a cryomicrotome (CM 3050; Leica) were incubated in blocking buffer (3% bovine serum albumin, 0.1% Triton X-100 in PBS, pH 7.4) for 20 min at room temperature. The sections were then incubated for 1 h at room temperature with either one of the primary antibodies for SGLT1 (ab126853; Abcam), NHE3 (custom antibody services; Thermo Fisher Scientific), DRA (PA5-68530; Thermo Fisher Scientific) or PAT1 (sc-26728; Santa Cruz Biotechnology) at 1:400 dilution. Alexa Fluor [488 nm green (A11078)] for SGLT1 and DRA and Alexa Fluor [488 nm green (A11036) for PAT1, and 568 nm red (A11072) for NHE3 secondary antibody (all obtained from Thermo Fisher Scientific)] were used at 1:800 dilution for 1 h at room temperature. Sections were then washed thrice in PBS, and the nucleus was stained with DAPI mount [i.e., Fluoroshield mounting medium with DAPI (ab104139; Abcam)] and observed with the EVOS FL Cell Imaging System (Thermo Fisher Scientific). Images were quantified by using Alpha View software (ProteinSimple).

Protein assay. Proteins were quantified with the DC Protein Assay Kit (Lowry method) according to the manufacturer's protocols (Bio-Rad, Hercules, CA, USA).

Statistics. Results presented represent means±SE of experiments performed and calculated by GraphPad Prism 7. All uptakes were done in triplicates. Student's t tests were performed for statistical analysis.

Abbreviations. BBM, brush border membrane; BBMV, BBM vesicle; BLM, basolateral membrane; DIDS, 4,4-diisothiocyanatostilbene-2,2-disulfonic acid disodium salt; DRA, down-regulated in adenoma; IEC-18, intestinal epithelial cell; LZR, lean Zucker rat; NHE3, Na—H exchange 3; ODHT, obesity, diabetes, and hypertension triad; OMG, O-methyl glucose; OZR, obese Zucker rat; SGLT1, Na-glucose cotransport 1; siRNA, small interfering RNA; SLC, solute carrier; TOM, TallyHo/JngJ mice.

Results

Figure 1B:
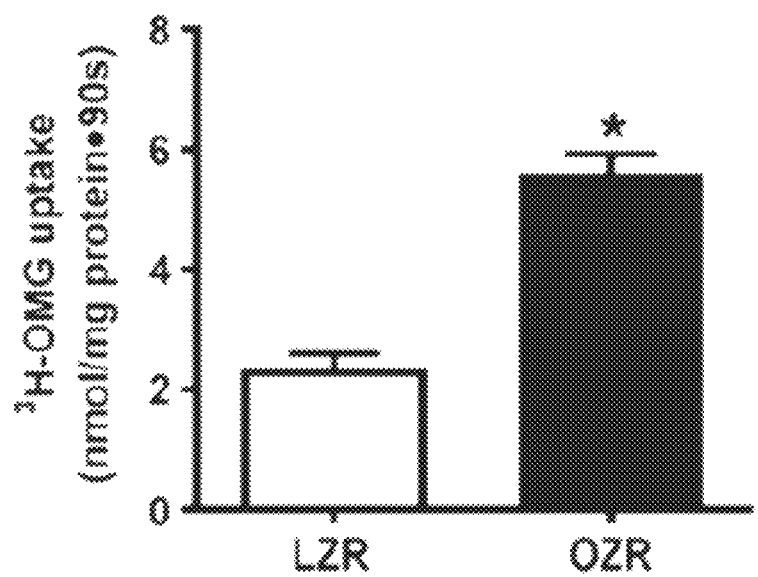
Figure 1C:
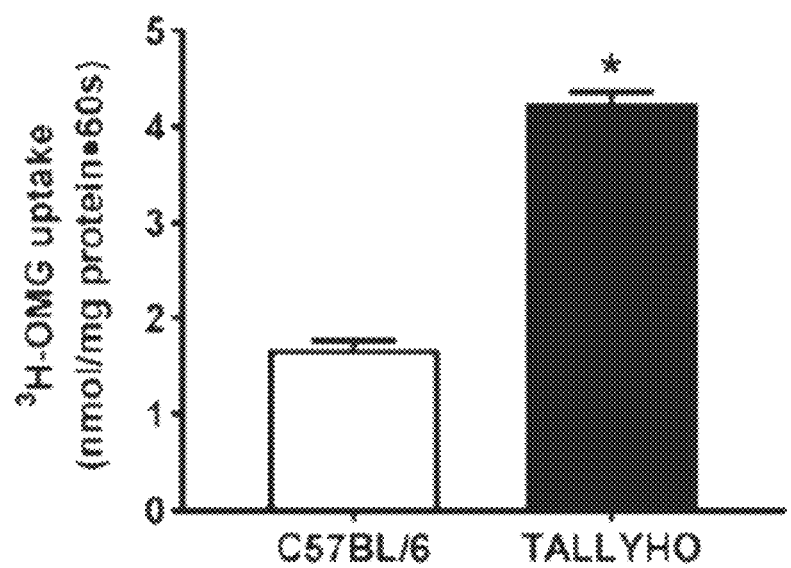
Figure 1D:
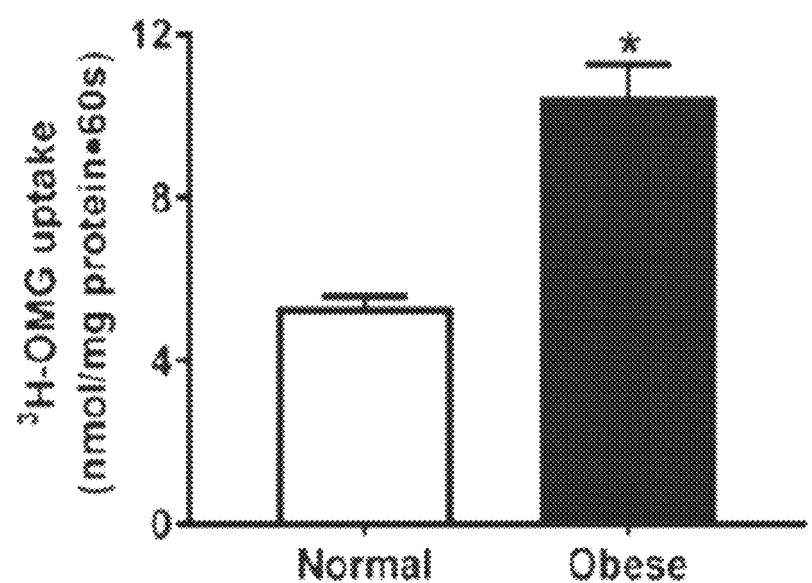
Figure 2A:
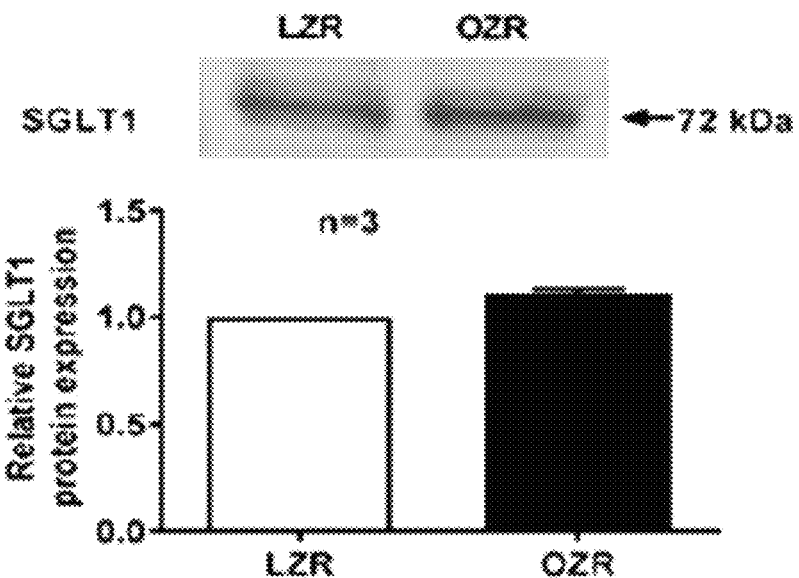
FIGS. 2A-2F include graphs and images showing the effect of obesity on SGLT1 protein, including: graphs and images of the results of western blot analysis showing that villus-cell SGLT1 protein levels remained unchanged in BBM between OZRs and LZRs (FIG. 2A), TOM and C57BL/6 (FIG. 2B), and obese and normal humans (FIG. 2C); and images and a graph of immunofluorescence studies of small-intestinal tissue sections showing that SGLT1 immunofluorescence with DAPI nuclear stain merged in LZRs (FIG. 2D) is unchanged in OZRs (FIG. 2E) and densitometric quantification of both (FIG. 2F) showed no change as well, where, in FIGS. 2A-2C, the upper panel is a representative Western blot experiment performed at least 3 times and quantitated in the lower panels, where a representative experimental pictograph is shown in FIGS. 2D-2E, and where quantitation of 5 such experiments is shown in FIG. 2F.
Figure 2B:
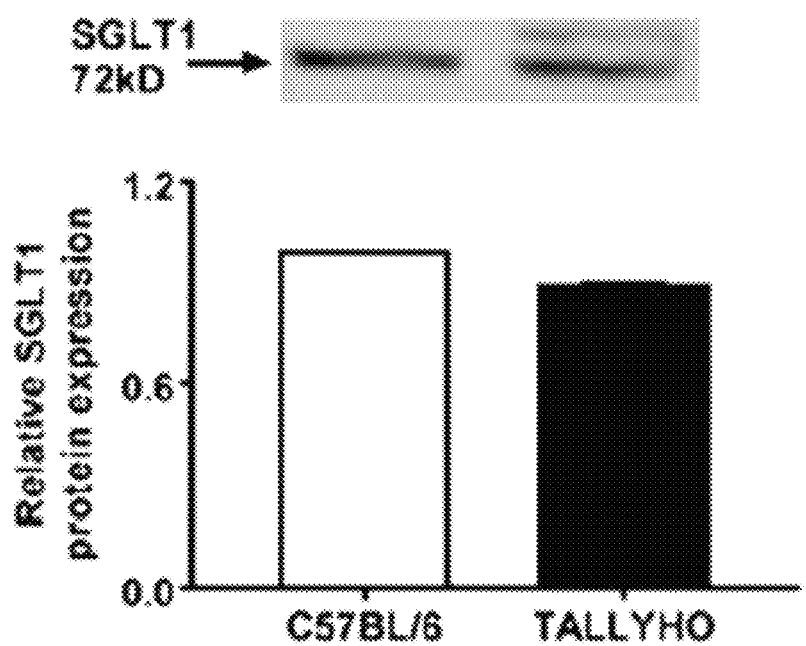
Figure 2C:
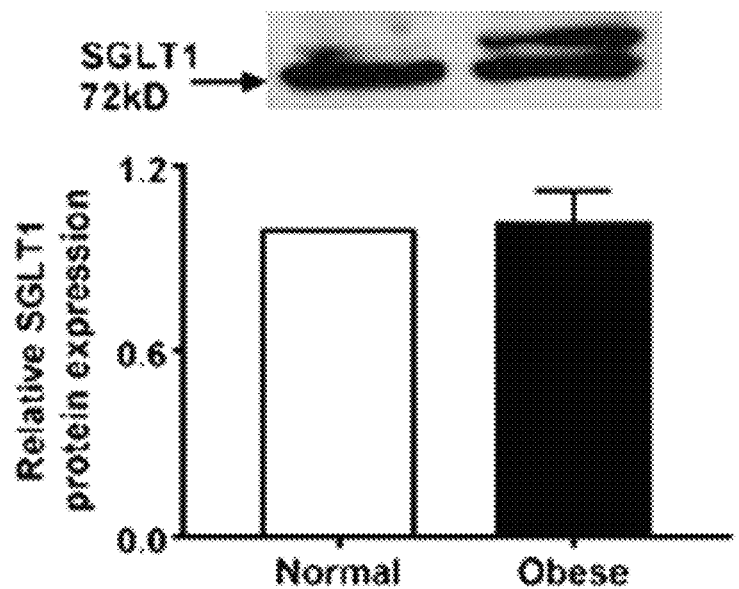
Figure 2D:
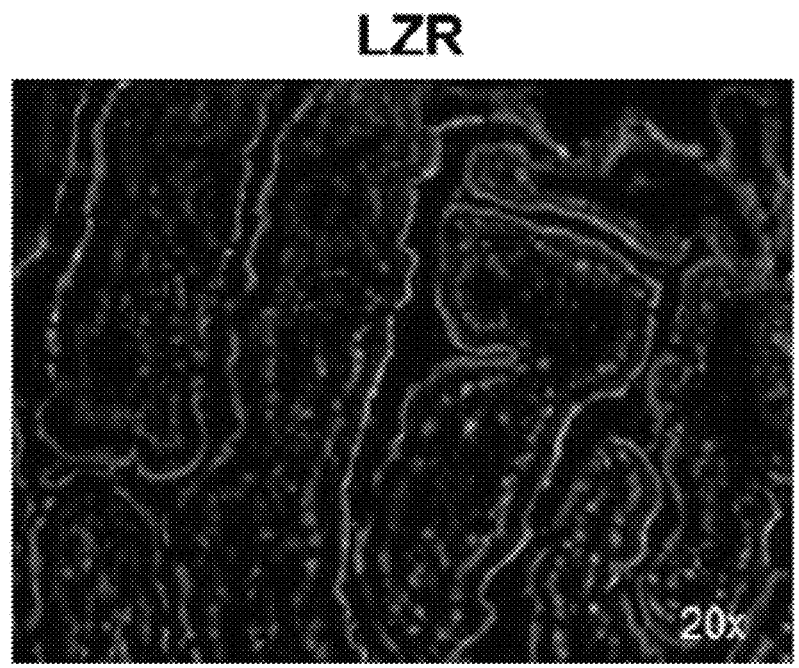
Figure 2E:
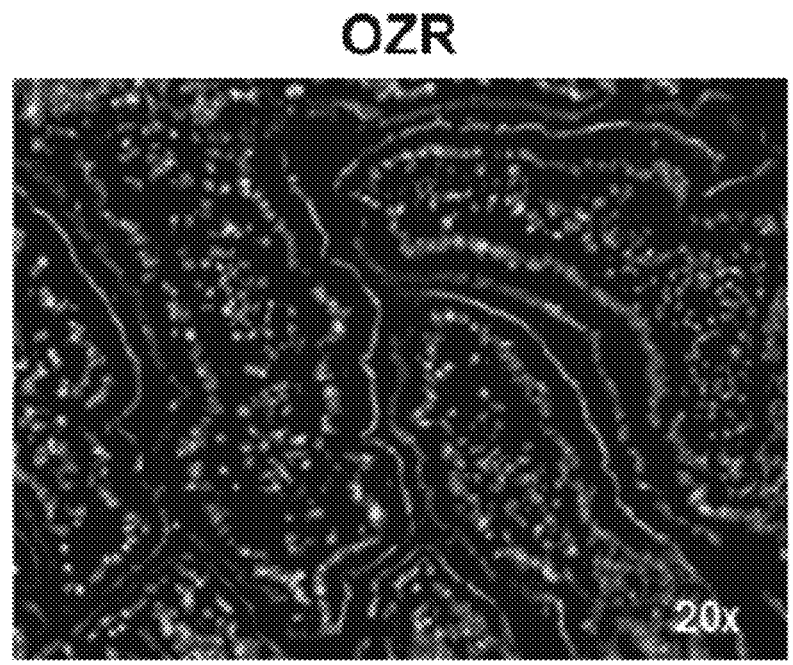
Figure 2F:
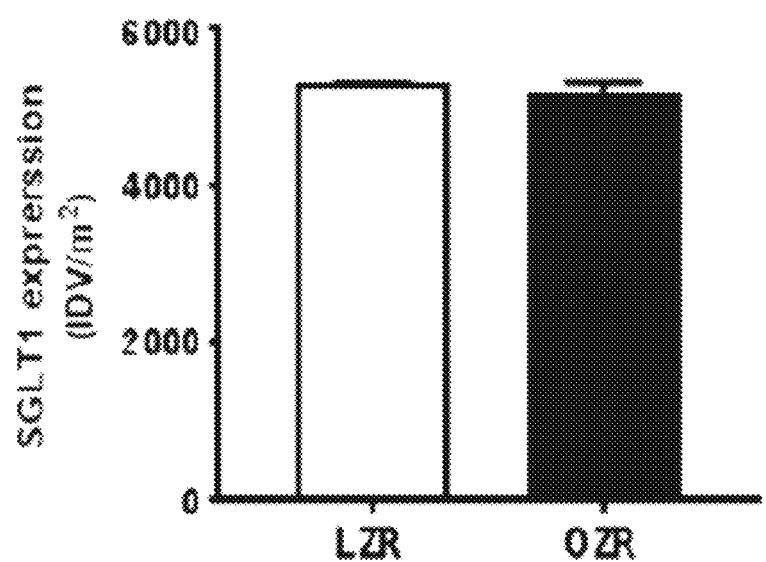

In intact villus cells isolated from obese Zucker rats (OZRs), SGLT1 activity, defined as phloridzin-sensitive Na-dependent uptake of 3-OMG, was stimulated (FIG. 1A). SGLT1 was also increased in villus-cell BBMV from OZRs (FIG. 1B). Illustrating broad applicability, SGLT1 was also increased in TOM (FIG. 1C) and obese humans (FIG. 1D). The mechanism of stimulation of SGLT1 was secondary to increased affinity (1/km) of the cotransporter for glucose [OZR: 4.8±0.4 mM; lean Zucker rat (LZR): 9±1; n=4, P<0.05)] without a change in the maximal rate of uptake of glucose ($V_{max}$, OZR: 2.1±0.1 nmol/mg pro/30 s; LZR: 1.9±0.1). Consistent with this, SGLT1 protein expression was unchanged in villus cells from OZRs (FIG. 2A), TOM (FIG. 2B), or obese humans (FIG. 2C). Further, immunofluorescence studies of small intestines showed that SGLT1 immunofluorescence (green) with DAPI nuclear stain (blue) merged in LZRs (FIG. 2D) was unchanged compared with OZRs (FIG. 2E). Relative fluorescence intensity quantifications confirmed this (FIG. 2F). Collectively and broadly, these data demonstrate that, during obesity, SGLT1 was stimulated secondary to an increase in the affinity for glucose without altered SGLT1 expression.

Figure 3A:
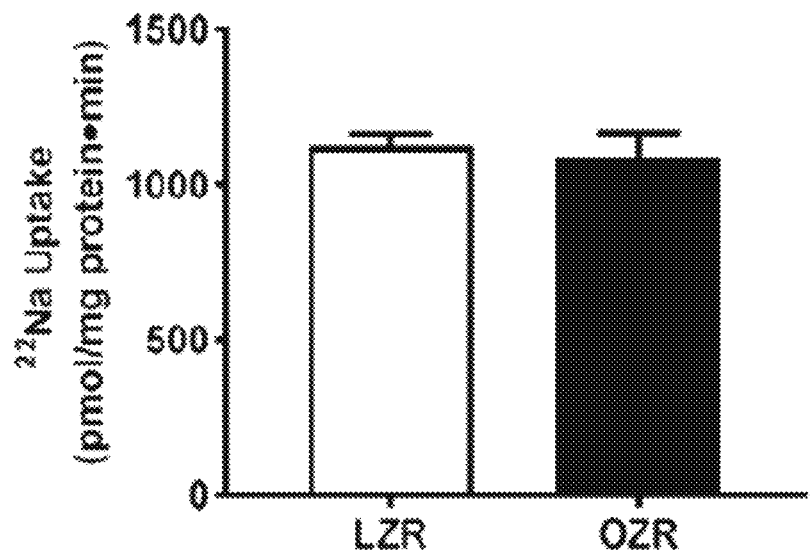
FIGS. 3A-3I include graphs and images showing Na—H exchange in intestinal epithelial cells in obesity, including: graphs showing NHE3, defined as 5-(N-ethyl-N-isopropyl) amiloride-sensitive and proton gradient-driven $^{22}$Na uptake, was unchanged in BBMVs from OZRs compared with LZRs (FIG. 3A) and showing that those observations were consistent in the BBMV preparations in TOM (FIG. 3B) and obese humans (FIG. 3C); graphs and images showing (FIGS. 3D-3F) western blot analysis revealing that villus-cell NHE3 protein levels remained unchanged in BBM between OZRs and LZRs (FIG. 3D), TOM and C57BL/6 (FIG. 3E), and obese and normal humans (FIG. 3F), and graphs and images showing that immunofluorescence studies for NHE3 expression in Zucker rats followed by densitometric analysis confirmed that NHE3 was unaltered between LZRs (FIG. 3G) and OZRs (FIG. 3H) in the BBM of small-intestinal villus cells, and that densitometric quantification of both (FIG. 3I) showed unchanged NHE3 as well, where, for all experiments, n represents different studies performed with intestinal cells isolated from different host each time, where in FIGS. 3D-3F, the upper panel is a representative Western blot experiment performed at least 3 times and quantitated in the lower panels, and where a representative experimental pictograph is shown in FIGS. 3G and 3H, and quantitation of 5 such experiments is shown in FIG. 3I; n=4. $P<0.01$ in graphs.
Figure 3B:
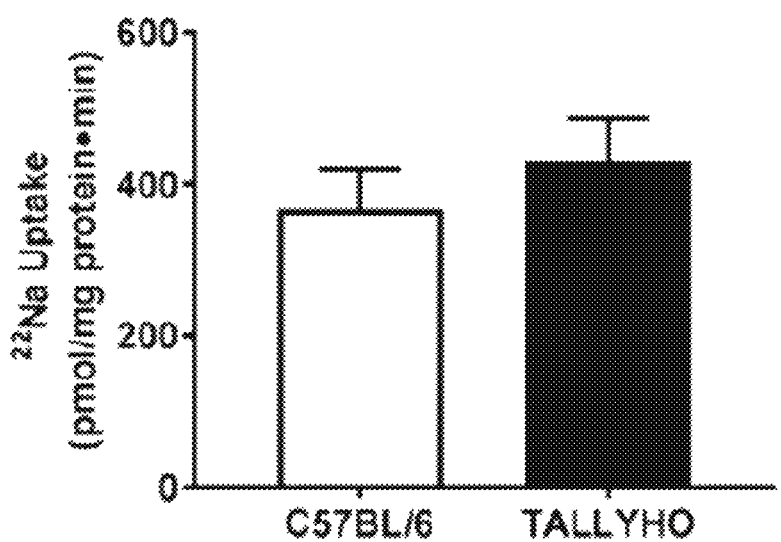
Figure 3C:
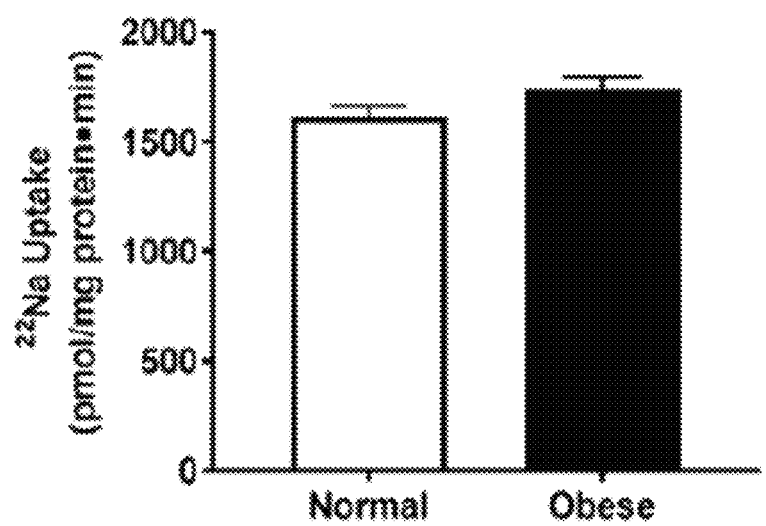
Figure 3D:
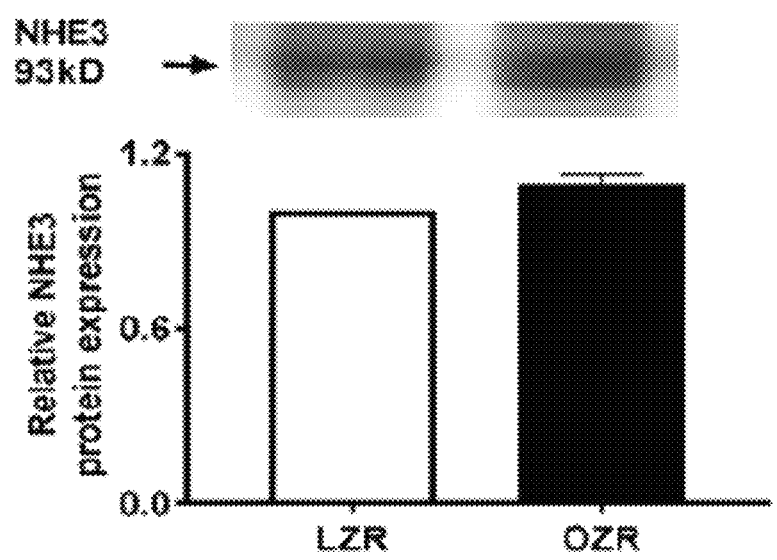
Figure 3E:
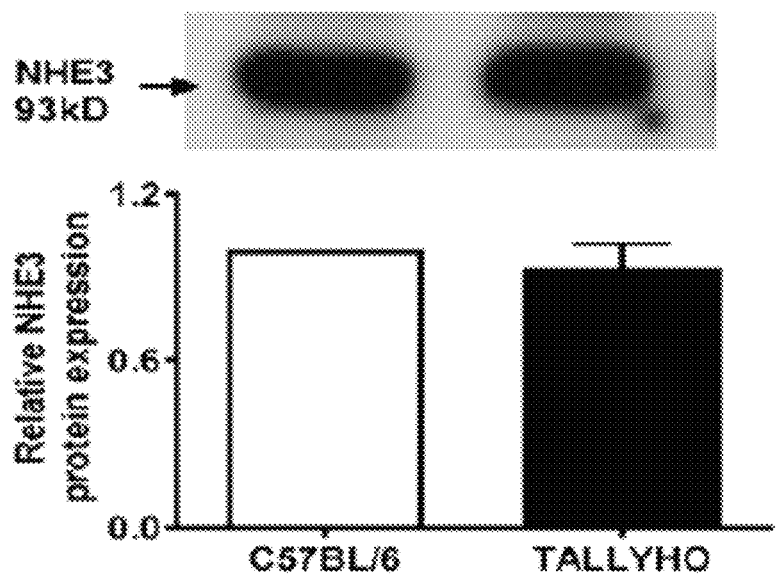
Figure 3F:
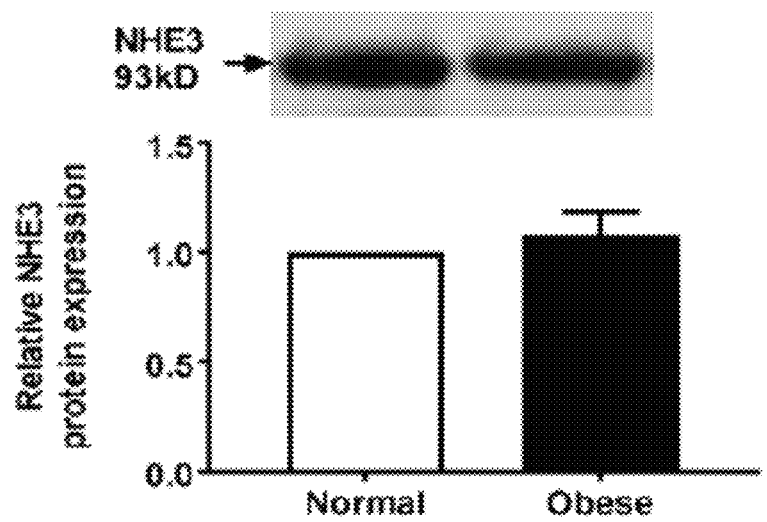
Figure 3G:
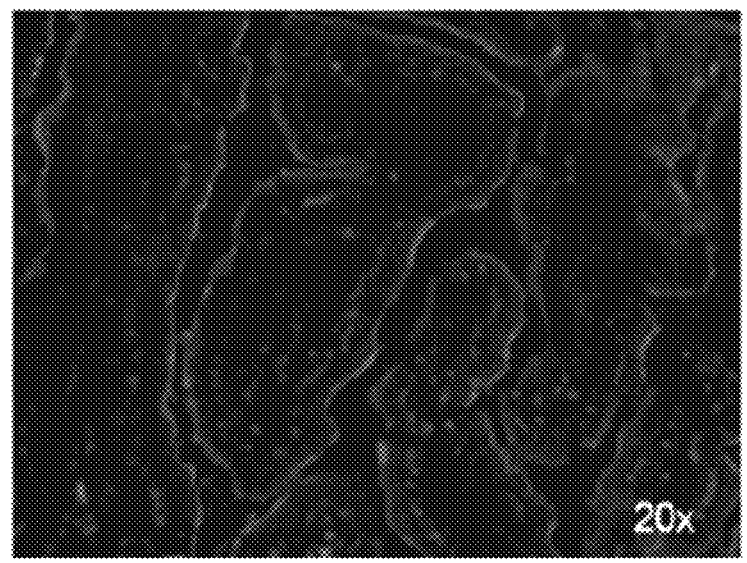
Figure 3H:
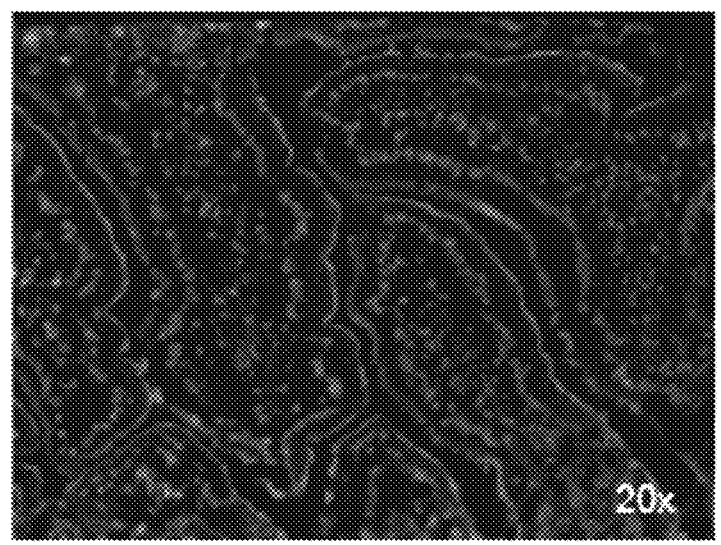
Figure 3I:
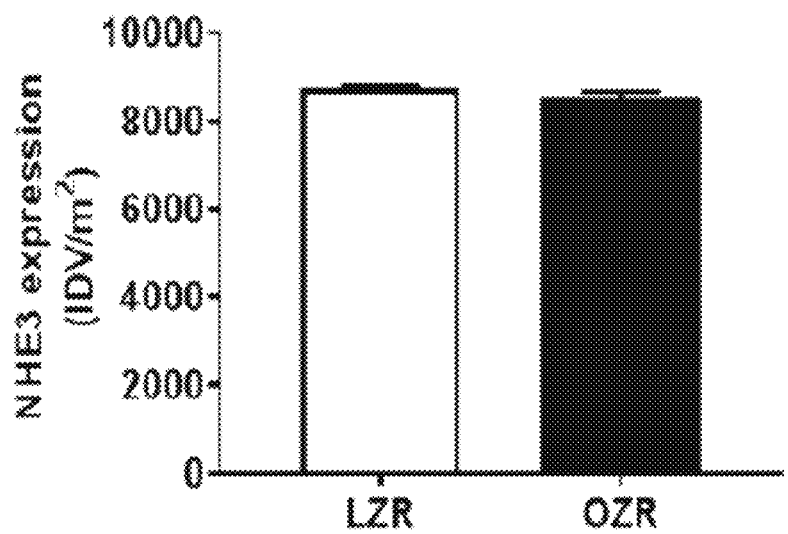

In contrast to the stimulation of SGLT1, NHE3, which with Cl—$HCO_3$ exchange promotes coupled NaCl absorption, was unaffected in villus-cell BBMV in OZRs (FIG. 3A), TOM (FIG. 3B), and obese humans (FIG. 3C). NHE3 protein expression was also unaltered in OZRs (FIG. 3D), TOM (FIG. 3E), and obese humans (FIG. 3F). Further, immunofluorescence studies in Zucker rats confirmed that NHE3 expression (red) was unaltered between LZRs and OZRs in small-intestinal villus cells (FIGS. 3G-3I). In obesity, villus cell-neutral NaCl absorption is not changed because the NHE3 that mediates it (along with Cl:$HCO_3$) is unaffected. Thus, altered NaCl homeostasis, important for hypertension, was likely not via altered neutral NaCl absorption in obesity.

Figure 4A:
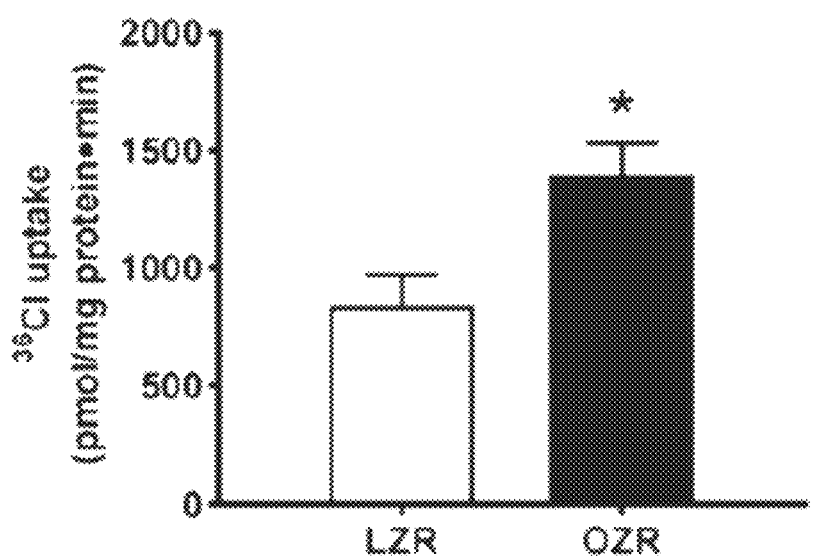
FIGS. 4A-4C are graphs showing the effect of obesity on Cl—HCO$_3$ exchange in intestinal epithelial cells, where DIDS-sensitive and HCO$_3$-driven $^{36}$Cl uptake was significantly increased in villus-cell BBMVs of OZRs as compared with LZRs (FIG. 4A), TOM vs. C57BL/6 (FIG. 4B), and obese human small intestine vs. normal (FIG. 4C), and where, for all experiments, n represents different studies performed with intestinal cells isolated from different host each time; n=4. *$P<0.01$.
Figure 4B:
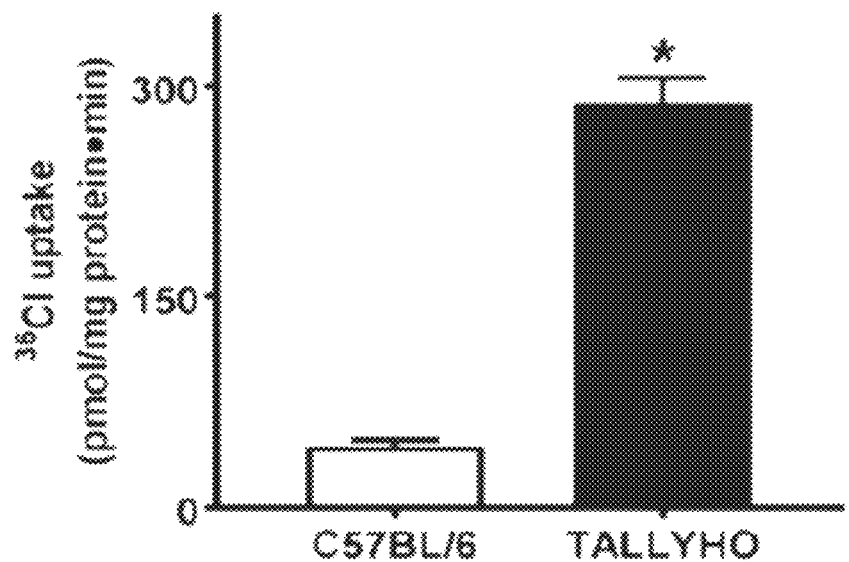
Figure 4C:
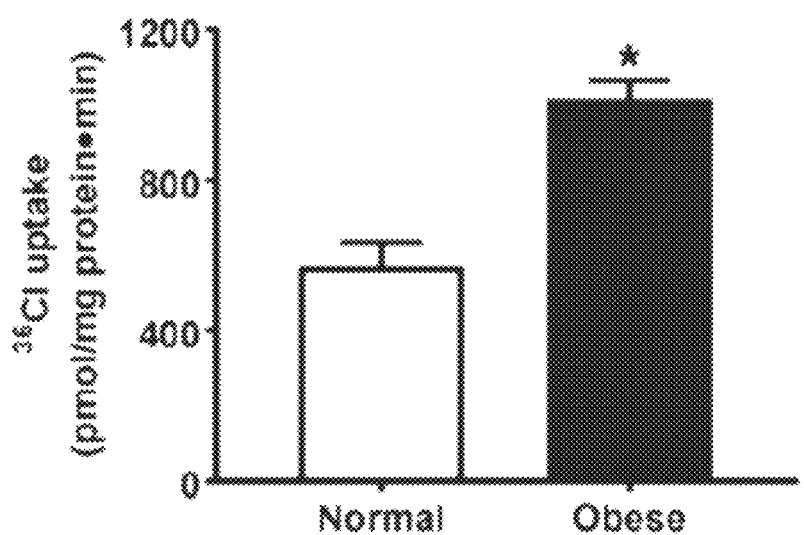
Figure 5A:
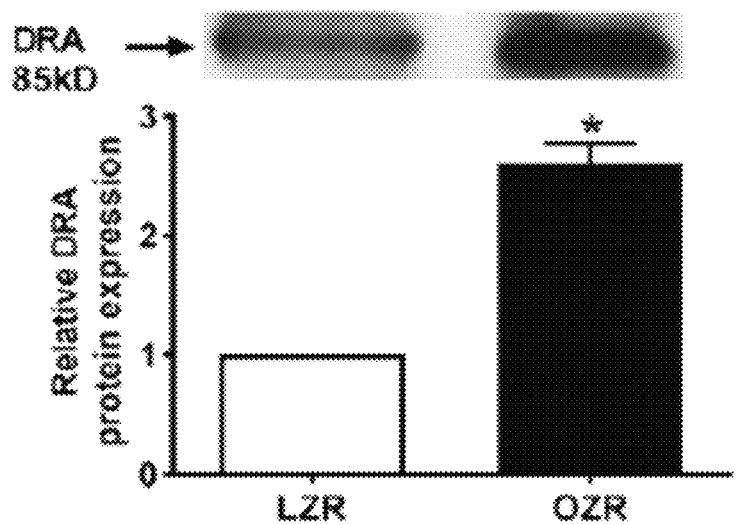
FIGS. 5A-5F are graphs and images showing the effect of obesity on DRA protein, where, in all 3 species, small-intestinal Cl—HCO$_3$ is mediated by DRA and PAT1, including: images and graphs showing, by Western blot analysis, BBM protein expression of DRA increased significantly in OZRs (FIG. 5A), TOM (FIG. 5B), and obese humans (FIG. 5C) compared with their respective controls, where western blot experiments were performed at least 3 times and quantitated in the lower panels; images and graphs showing that immunofluorescence studies in Zucker rats also showed that DRA expression was increased in LZRs (FIG. 5D) compared with OZRs (FIG. 5E) in the BBM of small-intestinal villus cells, and densitometric quantification of both (FIG. 5F) showed increased DRA during obesity as well, where, in FIGS. 5D and 5E, a representative experimental pictograph is shown, and quantitation of 5 such experiments is shown in F. *$P<0.01$.
Figure 5B:
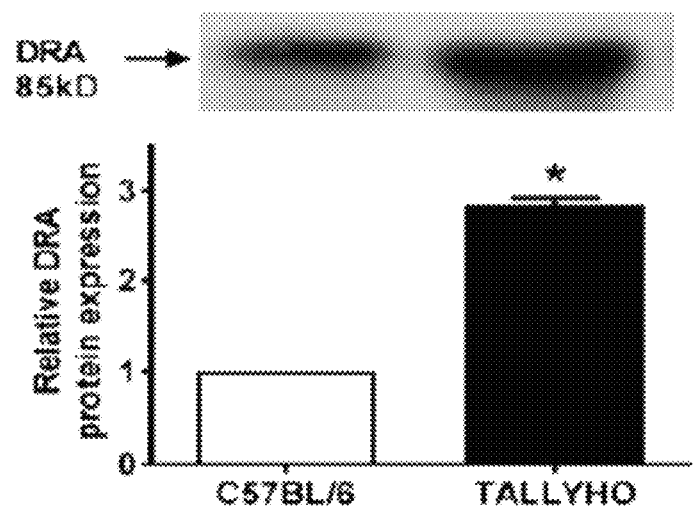
Figure 5C:
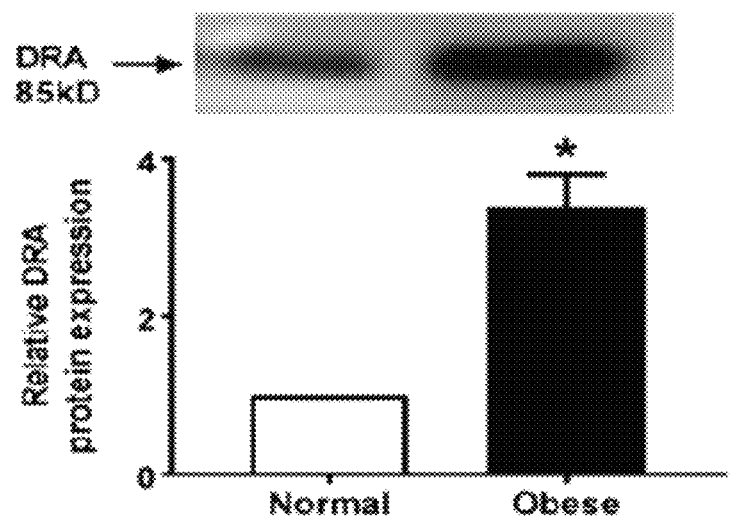
Figure 5D:
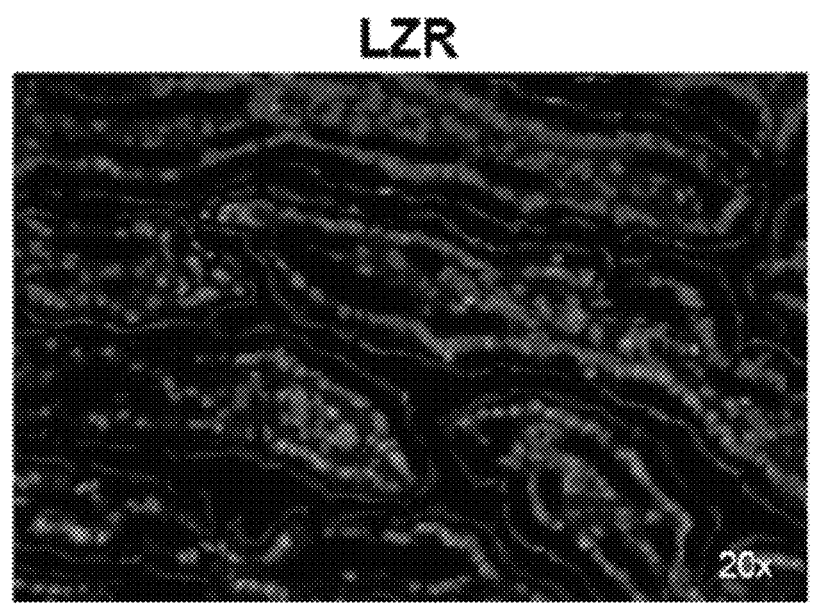
Figure 5E:
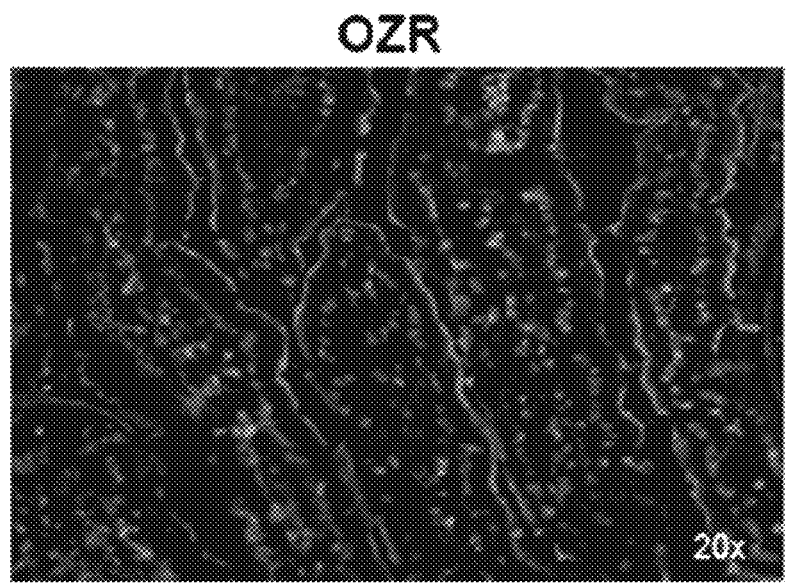
Figure 5F:
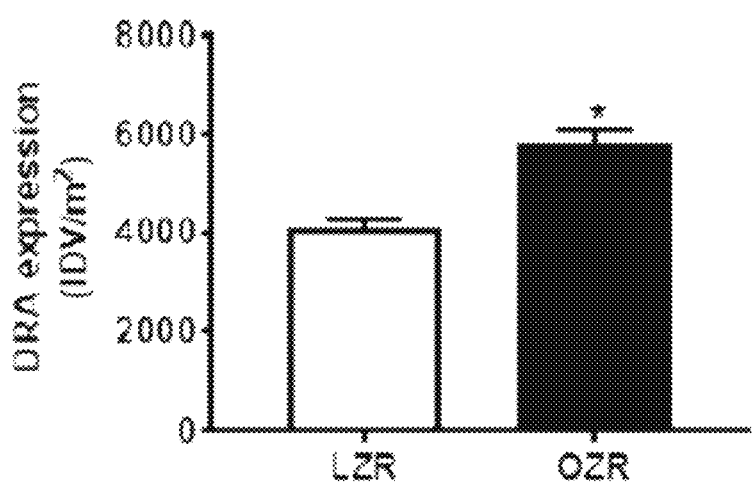
Figure 6A:
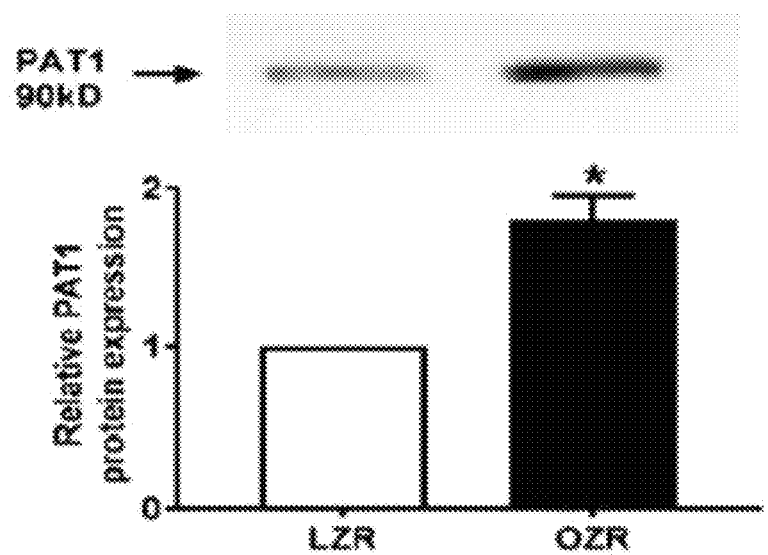
FIGS. 6A-6F are images and graphs showing the effect of obesity on PAT1 protein, including: images and graphs showing BBM protein expression of PAT1 increased significantly in OZRs (FIG. 6A), TOM (FIG. 6B), and obese humans (FIG. 6C) compared with their respective controls, where western blot experiments were performed at least 3 times and quantitated in the lower panels; and images and a graph showing that immunofluorescence studies in Zucker rats also showed that PAT1 expression (green) was increased in LZRs (FIG. 6D) compared with OZRs (FIG. 6E) in the BBM of small-intestinal villus cells, and that densitometric quantification of both (FIG. 6F) showed increased PAT1 during obesity as well, where, in FIGS. 6D and 6E, a representative experimental pictograph is shown and quantitation of 5 such experiments is shown in FIG. 6F. *$P<0.01$.
Figure 6B:
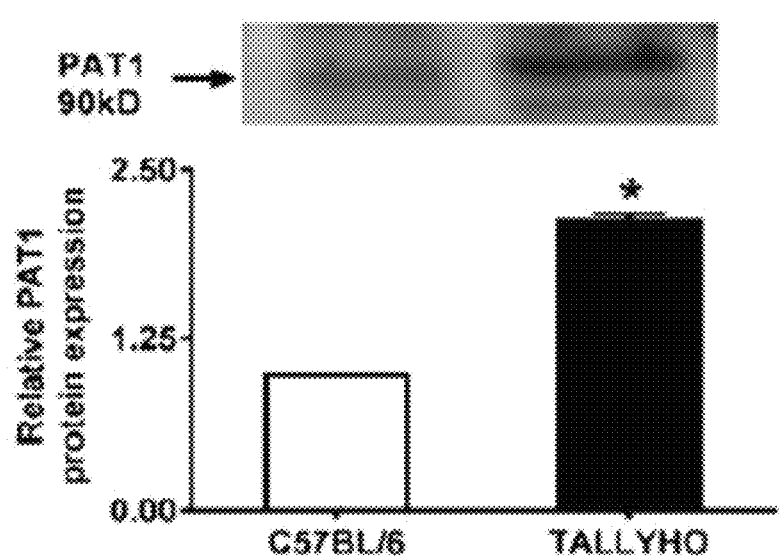
Figure 6C:
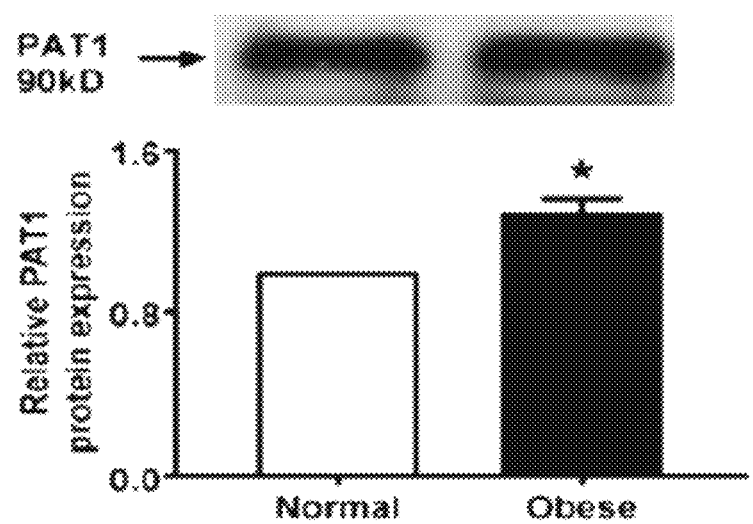
Figure 6D:
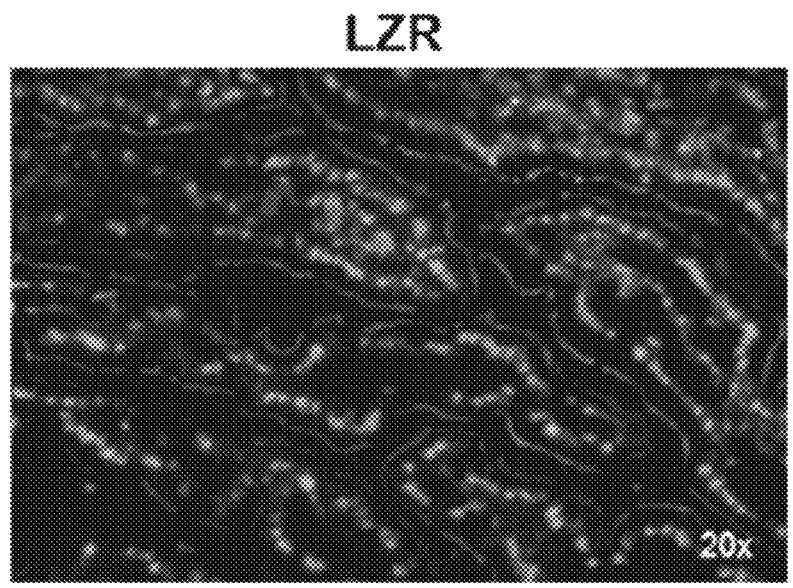
Figure 6E:
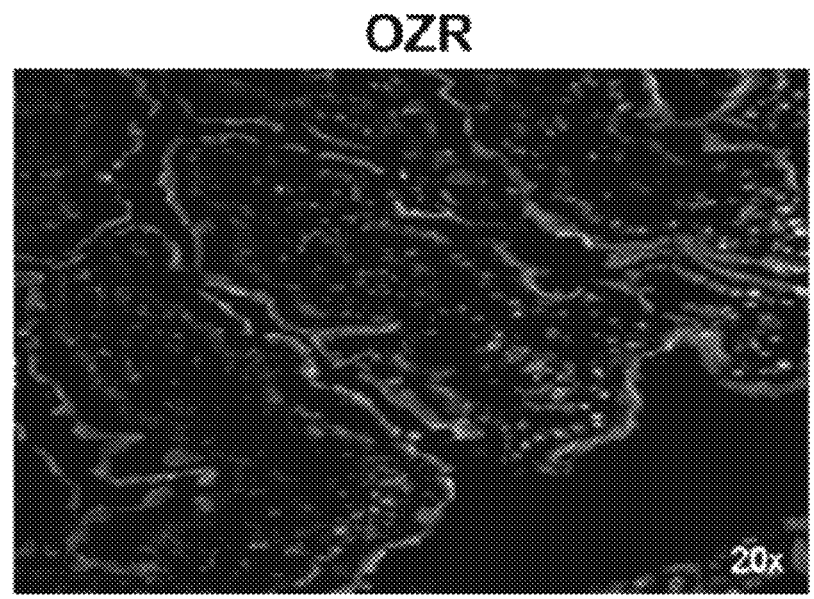
Figure 6F:
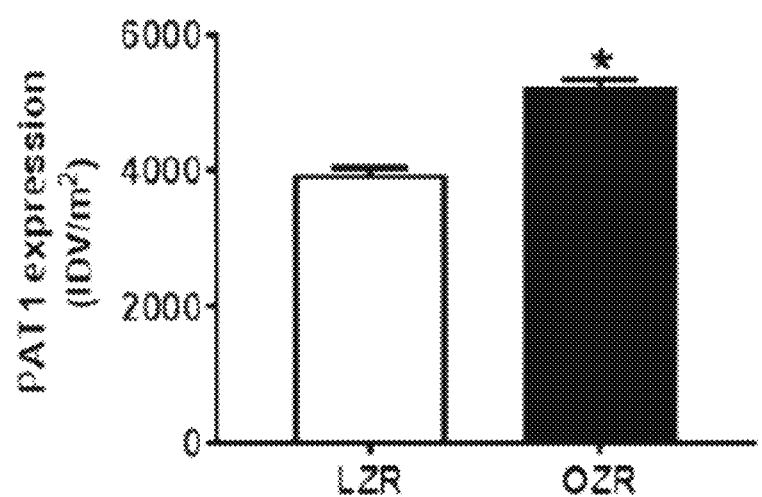

However, Cl—$HCO_3$ exchange, mediated by DRA and PAT1, was stimulated in villus-cell BBMV from OZRs (FIG. 4A), TOM (FIG. 4B), and obese humans (FIG. 4C). The mechanism of stimulation of Cl—$HCO_3$ exchange in OZRs was secondary to increased $V_{max}$ (OZR: 2.7±0.2 nmol/mg pro/12 s; LZR: 1.7±0.2; n=3, P<0.05) without altered $K_m$ (OZR: 6.3±0.4 mM; LZR: 6.2±0.5). Consistent with this, Western blot studies showed an increase in villus-cell BBM DRA protein in OZRs (FIG. 5A), TOM (FIG. 5B), and obese humans (FIG. 5C). Similarly, villus cell BBM PAT1 was also increased in OZRs (FIG. 6A), TOM (FIG. 6B), and obese humans (FIG. 6C). Further, immunofluorescence studies showed that DRA expression (green) was increased in OZRs (FIG. 5E) compared with LZRs (FIG. 5)) in the BBM of small intestinal villus cells during obesity (FIGS. 5D-5F). Similarly, PAT1 expression (green) was also increased in OZRs (FIG. 6E) compared with LZRs (FIG. 6D) in the BBM of small-intestinal villus cells in obesity (FIGS. 6D-6F). Thus, in obesity, BBM Cl—$HCO_3$ exchange is stimulated secondarily to increased BBM DRA and PAT1 without altered affinity of the exchangers. Together, these data show that, in obesity, despite unaltered NHE3, Cl—$HCO_3$ exchange is stimulated. Thus, although traditional coupled NaCl absorption is maintained, novel coupling of DRA or PAT1 with SGLT1 additionally enhances NaCl absorption in obesity in rats, mice, and humans.

Figure 7A:
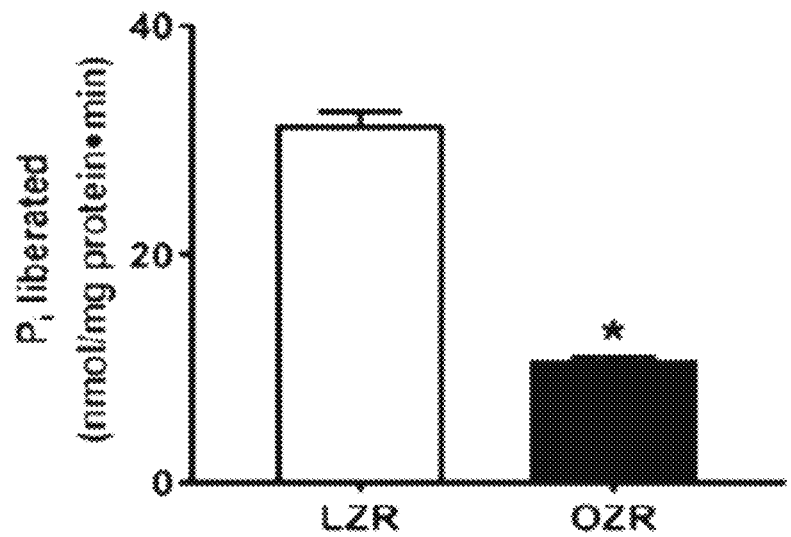
FIGS. 7A-7J are graphs, images, and a schematic diagram showing obesity-mediated alterations in Na/K-ATPase activity in intestinal epithelial cells, including: graphs showing Na/K-ATPase activity was significantly reduced in villus-cell homogenates obtained from OZRs vs. LZRs (FIG. 7A), TOM vs. C57BL/6 (FIG. 7B), and obese human small intestine vs. normal (FIG. 7C), graphs showing that transfection with siRNA for Na/K-ATPase-a1 subunit (siNa/K-ATPase-a1) in rat intestinal epithelial cells significantly stimulated Na-glucose cotransport (FIG. 7D), whereas Na—H exchange remained unaffected (FIG. 7E) as previously demonstrated and reproduced here; a graph showing that Cl—HCO$_3$ exchange was also stimulated (FIG. 7F) in siNa/K-ATPase-a1 IEC-18 cells; graphs and images showing that the BBM protein expression of the C—HCO$_3$ exchangers, DRA (FIG. 7G) and PAT1 (FIG. 7H), was significantly increased in siNa/K-ATPase-a1 IEC-18 cells compared with controls (FIG. 7I); and a schematic diagram showing a proposed model of deregulation of glucose and Na homeostasis in obesity (FIG. 7J), where the diagram depicts normal mammalian intestinal epithelial cells with traditional coupled NaCl absorption via coupling of BBM Na—H and Cl—HCO$_3$ exchange, BBM Na-glucose cotransport and BLM Na/K-ATPase (left panel), and depicts alterations in obesity (right panel) showing inhibition of BLM Na/K-ATPase stimulating BBM Na-glucose cotransport and Cl—HCO$_3$ exchange, resulting in a novel mechanism of stimulated NaCl absorption, whereas traditional coupled NaCl absorption is maintained, thus resulting in deregulation of glucose and Na homeostasis seen in obesity, where all observations are consistent with the observations from all 3 in vivo models of obesity, where, for all experiments, n represents different studies performed with intestinal cells isolated from different host each time, where all experiments in FIGS. 7D-7H were consistently reproduced at least 3 times, each time with transfected IEC-18 cells revived from a different frozen stock, and where in FIGS. 7G-7H, the upper panel is a representative Western blot experiment performed at least 3 times and quantitated in the lower panels; n=4; pi, $P<0.01$. *$P<0.01$.
Figure 7B:
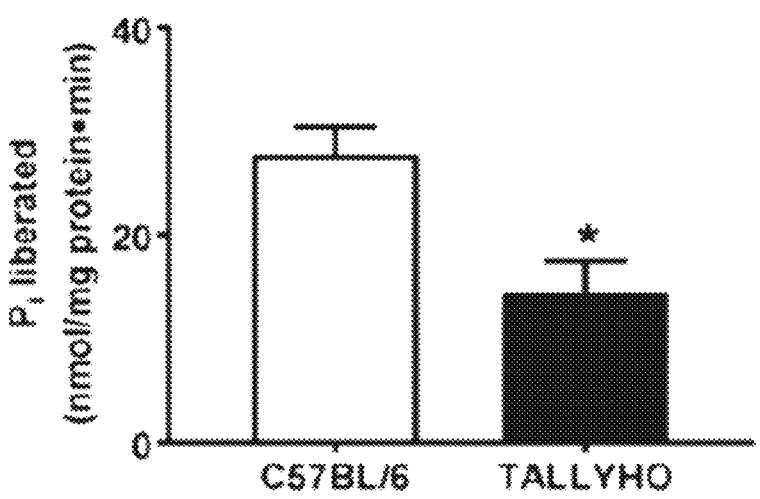
Figure 7C:
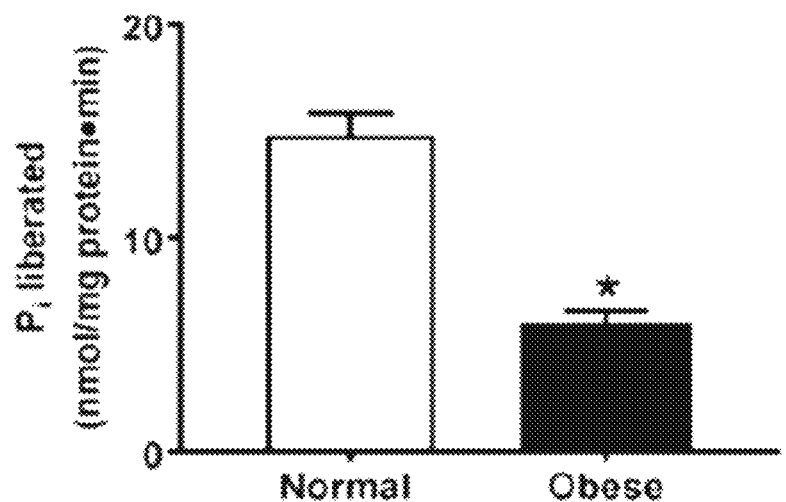

Stimulation of SGLT1 in intact villus cells (FIG. 1A) during obesity was believed to be, at least in part, due to enhanced BLM Na/K-ATPase activity. However, Na/K-ATPase was reduced in villus cells in OZRs (FIG. 7A), TOM (FIG. 711), and obese humans (FIG. 7C).

Figure 7D:
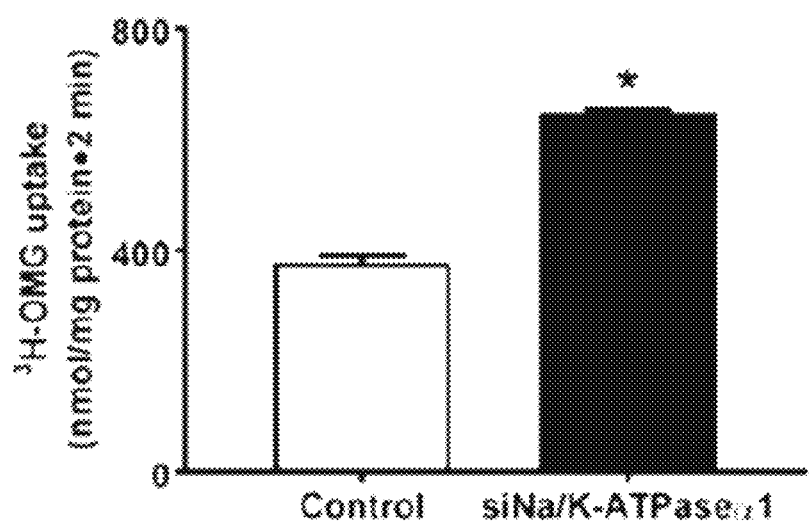
Figure 7E:
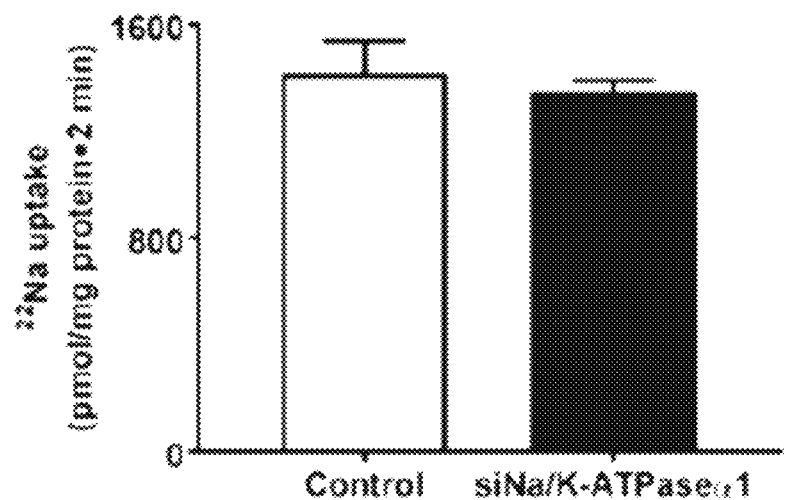
Figure 7F:
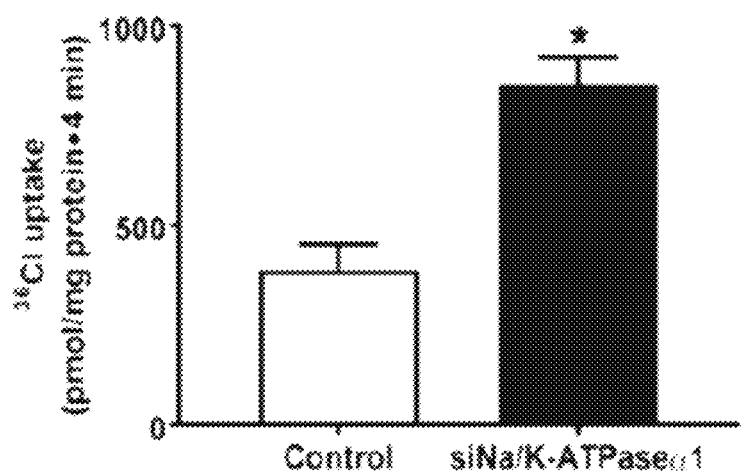
Figure 7G:
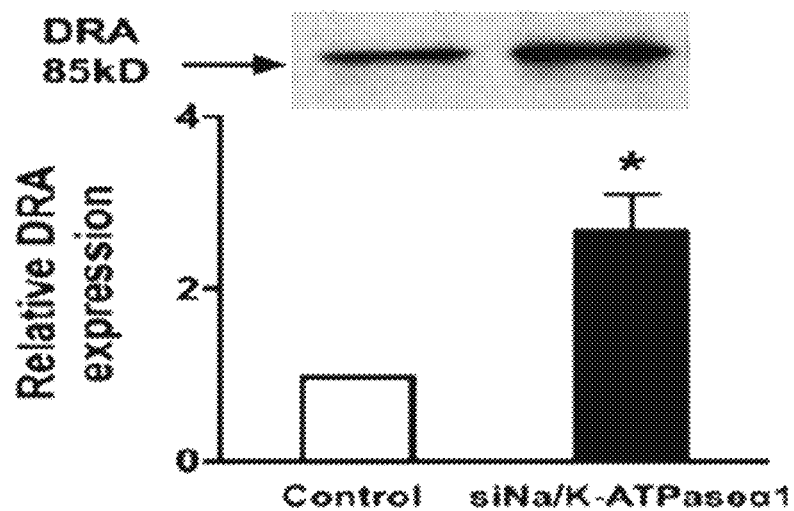
Figure 7H:
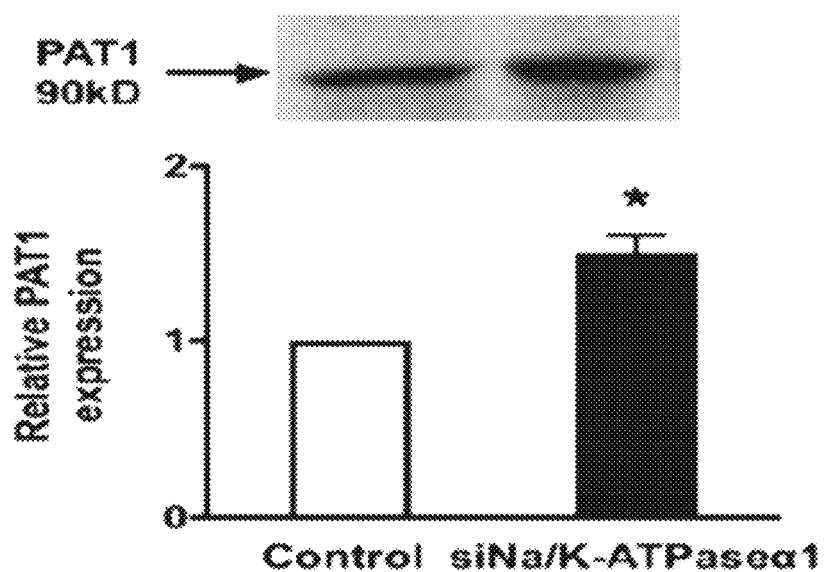
Figure 7I:
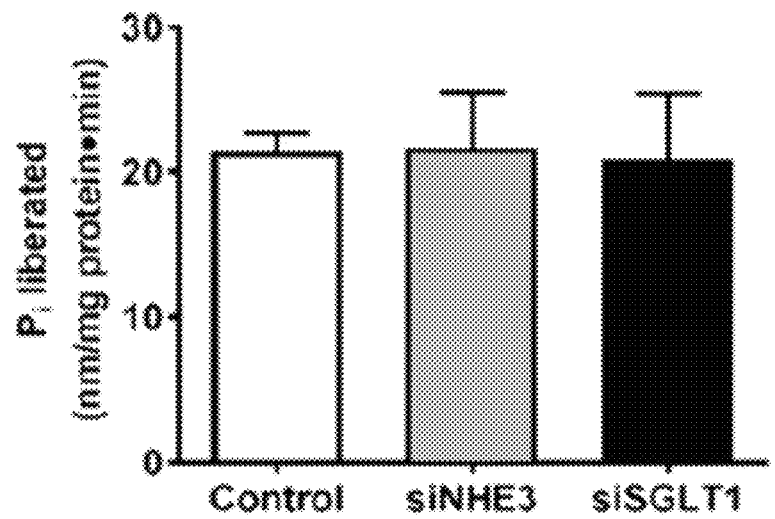
Figure 7J:
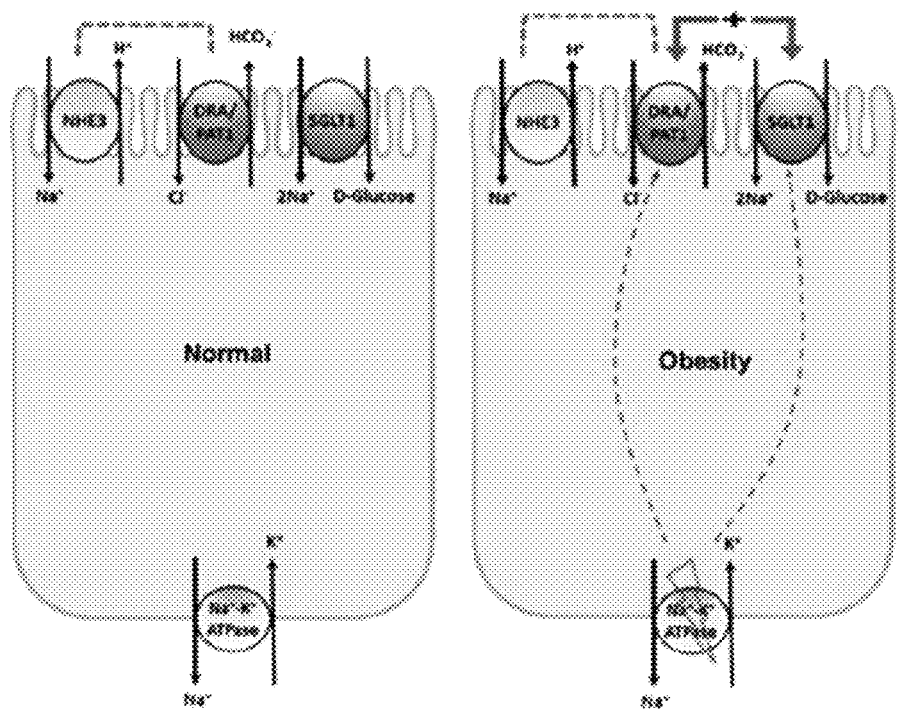

To test that hypothesis, that primary inhibition of Na/K-ATPase leads to enhanced glucose and NaCl absorption, Na/K-ATPase was directly inhibited with siRNA for its α1-subunit in IEC-18 cells. In these experiments, SGLT1 was stimulated (FIG. 7D). The mechanism of stimulation was identical to that seen in vivo in all 3 obesity models: enhanced affinity for glucose without a change in BBM cotransporter numbers. Further, NHE3 was unaffected (FIG. 7E) in these cells. Finally, similar to in the obesity models, Cl:HCO$_3$, mediated by DRA and PAT1, was stimulated (FIG. 7F) in these cells. The mechanism of stimulation was again increased V$_{max}$ (siRNA: 74±1.2 pmol/mg pro/30 s; control: 53.4±0.5; n=3, P<0.05) without altered K$_m$ (siRNA: 3.5±0.1 mM; control:3.7±0.1). Consistent with this, Western blot studies showed increased DRA (FIG. 7G) and PAT1 (FIG. 7H) expression in these cells. To determine whether inhibition of either BBM NHE3 or SGLT1 may affect BLM Na/K-ATPase, these 2 BBM transporters were silenced, and the activity of Na/K-ATPase was determined. As shown in FIG. 7I, silencing the BBM NHE3 or SGLT1 had no effect on BLM Na/K-ATPase. These data indicate that an initial direct and specific reduction in intestinal epithelial cell BLM Na/K-ATPase results in the novel stimulation and coupling of BBM SGLT1 and DRA or PAT1, promoting the enhanced glucose and NaCl absorption in obese rats, mice, and humans (FIG. 7J).

Discussion

These studies indicate that in the obesity, diabetes, and hypertension triad, inhibition of intestinal villus-cell BLM Na/K-ATPase may be the initial pathophysiological alteration. Then, as compensation, BBM SGLT1 is likely stimulated. Furthermore, to maintain electro neutrality, DRA/PAT1 is also stimulated. This results in a novel additional mechanism of enhanced NaCl absorption during obesity. Further, because NHE3 is unaffected, traditional coupled NaCl absorption is also maintained. This novel coupling is twice as potent as the traditional one because SGLT1 absorbs 2 Na for each glucose and thus 2 Cl as well. Of course, stimulation of SGLT1 enhances glucose absorption as well (FIG. 7J). These observations are seen in 2 animal models of obesity and, most importantly, in human obesity as well. Further, specific RNA silencing in intestinal epithelial cells in vitro confirms the broad in vivo findings.

Therefore, these novel observations are believed to provide the pathophysiologic basis for the deregulation of NaCl and glucose homeostasis of hypertension and diabetes, respectively, in obesity. First, these studies show coupled NaCl absorption mediated by the dual operation of Na—H exchange (NHE3) and Cl—HCO$_3$ exchange (DRA or PAT1) appears to be unaffected and preserved in hypertension of obesity (FIG. 7J) because NHE3 is unaffected in OZR (FIG. 3A), Tallyho mouse (FIG. 3B), and obese human small intestine (FIG. 3C). However, a more potent and novel pathway of NaCl absorption appears to be the cause of Na homeostasis imbalance in obesity-associated hypertension.

In contrast to NHE3, the other most prominent Na absorptive pathway in the mammalian small intestine, namely SGLT1, was stimulated in villus-cell BBM in OZRs (FIGS. 1A-1B). Although the phenotype of these rats is comparable to human obesity with diabetes, hypertension, dyslipidemia, etc., it may be argued that the genotype, leptin knockout, does not have a human counterpart. Thus, a polygenic mouse model of obesity, TallyHo, was studied, and, again, here, SGLT1 was stimulated in the small intestine (FIG. C). SGLT1 was most tellingly stimulated in the small intestine of obese humans (FIG. 1D). The mechanism of stimulation of SGLT1 was not secondary to an increase in villus-cell BBM cotransporter numbers in Zucker rat, TallyHo mouse, or obese human intestine as demonstrated by Western blot studies (FIGS. 2A-2C). In agreement with these findings, immunofluorescence studies of OZRs and LZRs also did not show any change in SGLT1 expression (FIGS. 2D-2F). Consistent with all of these observations, kinetic studies demonstrated that, indeed, the mechanism of stimulation of SGLT1 in OZRs was secondary to an increase in the affinity of the cotransporter for glucose without a change in BBM cotransporter numbers.

Because SGLT1 stimulation was noted both at the level of the BBM as well as in intact cells from the obese intestine, Na/K-ATPase, which provides the favorable Na gradient for SGLT1, was studied. Contrary to the expectation that Na/K-ATPase may be increased to support the stimulated SGLT1, it was surprisingly diminished in Zucker rat villus cells (FIG. 7A). This unexpected observation was then confirmed in TallyHo mouse as well as in obese human small intestines (FIGS. 7B-7C). This led to the novel hypothesis that a primary inhibition of villus-cell BLM Na/K-ATPase in the obese intestine leads to a compensatory stimulation of BBM SGLT1 in these cells. To test this, Na/K-ATPase was directly inhibited in rat intestinal epithelial cells with siRNA for the α-subunit of Na/K-ATPase. This resulted in the inhibition of the activity of Na/K-ATPase in these cells similar to that seen in villus cells from the obese intestine of rats, mice, and humans. It was previously demonstrated that Na—H exchange, mediated by NHE3, was unaffected in these cells. However, SGLT1 was stimulated in these cells in a manner similar to that seen in obese animals and human. In fact, the mechanism of stimulation, secondary to an increase in the affinity of the cotransporter for glucose without an alteration in the number of cotransporters, was also identical to the mechanism of stimulation of SGLT1 in obese animals and humans. Taken together, these results supported the novel finding that, in obesity, a primary inhibition of BLM Na/K-ATPase in the absorptive villus cells leads to a compensatory stimulation of BBM SGLT1.

Intact tissue studies (e.g., Ussing-chamber studies) do not provide mechanistic information because they are made of villus and crypt cells, which are fundamentally different, as well as immune cells, fibroblasts, and enteric neurons, all of which can have an effect on transport. Thus, in the foregoing study, in all cases, ileal villus cells or BBMVs prepared from ileal enterocytes were used. Intact cells and BBMVs provide complementary mechanistic information. For example, as previously, discussed, at the level of the intact cell, BLM Na/K-ATPase has a regulatory role in the functioning of the BBM Na-dependent cotransporter. But in BBMV studies, one can decipher the effect purely at the level of the transporter without the influence of Na/K-ATPase and thus better define the mechanism of alteration. Similarly, this study concentrated on effects in the ileum. Although there is more absorption in the jejunum compared with the ileum, including via paracellular pathways and solvent drag, in the ileum, the transport is predominantly transcellular via enterocyte transporters, and that is why the studies were concentrated in this region of the gut.

Interestingly, stimulation of SGLT1 accelerates the intestinal glucose absorption that leads to excessive insulin release and fat deposition, resulting in decreased plasma glucose, which triggers repeated glucose intake and thus obesity. Conversely, obesity may be counteracted by inhibition of SGLT1. For example, SGLT1 knockout mice have been shown to have lower body weights, implying diminished glucose absorption leads to a lower body weight.

Not only does the stimulation of SGLT1 in obesity lead to enhanced glucose assimilation, it also leads to a significant increase in Na absorption because for every glucose molecule transported into the villus cells, 2 Na are also transported in the cells by SGLT1. This significant increase in positively charged Na would require a similar significant increase in Cl absorption to maintain electroneutrality. Indeed, when Cl—$HCO_3$ exchange activity was determined in OZRs, it was increased in the BBM of villus cells. Like SGLT1, Cl—$HCO_3$ exchange activity was also increased in Tallyho mouse intestine, and most importantly in the obese human intestine as well. Kinetic studies demonstrated that the mechanism of stimulation of Cl—$HCO_3$ in OZRs was secondary to an increase in the number of BBM transporters without a change in the affinity of the exchanger. Cl—$HCO_3$ exchange is mediated by DRA and PAT1 in rat, mouse, and human intestines. Consistent with kinetic studies, Western blot studies demonstrated an increase in both DRA and PAT1 in the intestines of OZRs, TallyHo mice, and, importantly, in humans as well. Taken together, stimulation of SGLT1 and DRA or PAT1 in absorptive villus cells during obesity means a new and significantly more potent means of increase in NaCl assimilation, leading to the altered NaCl homeostasis essential for hypertension seen in obesity.

Previously, it was hypothesized and confirmed with in vitro studies that a primary inhibition of BLM Na/K-ATPase activity leads to the compensatory increase in SGLT1 during obesity but not NHE3. However, the opposite, inhibition of neither BBM SGLT1 nor NHE3, affects BLM Na/K-ATPase. Thus, it was hypothesized that, in obesity, inhibition of Na/K-ATPase likely results in the stimulation of SGLT1 but not NHE3. To determine whether the de novo and more potent coupling of SGLT1 and DRA or PAT resulting in enhanced NaCl absorption is in fact present secondary to a primary inhibition of Na/X-ATPase, in vitro studies were carried out. Cl—$HCO_3$ exchange, mediated by DRA and PAT1, was stimulated in these cells in a manner similar to that seen in obese animals and humans. In fact, the mechanism of stimulation, secondary to an increase in the number of transporters without an alteration in the affinity of the exchanger for Cl, was also identical to the mechanism of stimulation of Cl—$HCO_3$ exchange in obese animals and humans. In these in vitro studies, scrambled controls were used, and transfection with them did not produce any nonspecific transporter effects. Further, siRNA transfection for the α1-subunit of Na/K-ATPase not only decreases mRNA expression by 60% at 4 d post-confluence but also the activity of Na/X-ATPase. Taken together, these results indicated that, in obesity, a primary inhibition of BLM Na/K-ATPase in the absorptive villus cells leads to a compensatory stimulation of BBM SGLT1 and DRA or PAT1, resulting in a de novo potent increase in NaCl assimilation during obesity.

Determination of the regulation of NHE3 and SGLT1 in obesity was made all the more interesting by the observation that mammalian intestinal BBBM NHE3 and SGLT1 can directly regulate one another. It was shown using siRNA to silence NHE3 or SGLT1 that silencing NHE3 significantly increased the SGLT1 activity, whereas inhibiting SGLT1 stimulated NHE3 in intestinal epithelial cells. This would suggest that, in obesity, where SGLT1 is stimulated, NHE3 should diminish. However, because NHE3 is unaffected, this mode of regulation between SGLT1 and NHE3 appears to be lost in obesity, thus potentially contributing to the enhanced NaCl absorption necessary for hypertension associated with obesity.

In summary, the novel observations of the foregoing study in multiple species including humans and confirmed by in vitro RNA silencing alter how we view the pathogenesis of the all-too-ubiquitous obesity, diabetes, and hypertension triad. In obesity, inhibition of BLM and Na/K-ATPase directly and selectively stimulates BBM SGLT1 with subsequent stimulation of BBM DRA or PAT1, which collectively results in stimulation of glucose and NaCl absorption. Taken together, these observations, broadly applicable in rats, mice, and humans, provide for the first time the mechanisms of enhanced intestinal glucose and NaCl absorption important for the pathogenesis of obesity-associated diabetes and hypertension.

Figure 8:
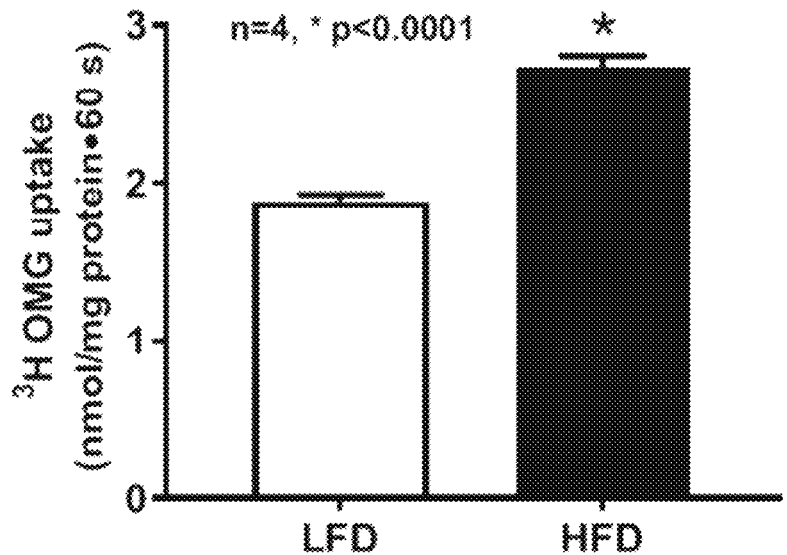
FIG. 8 is a graph showing Na-glucose co-transport uptake was significantly increased in villus cell BBM from HFD compared to LFD mice.
Figure 9:
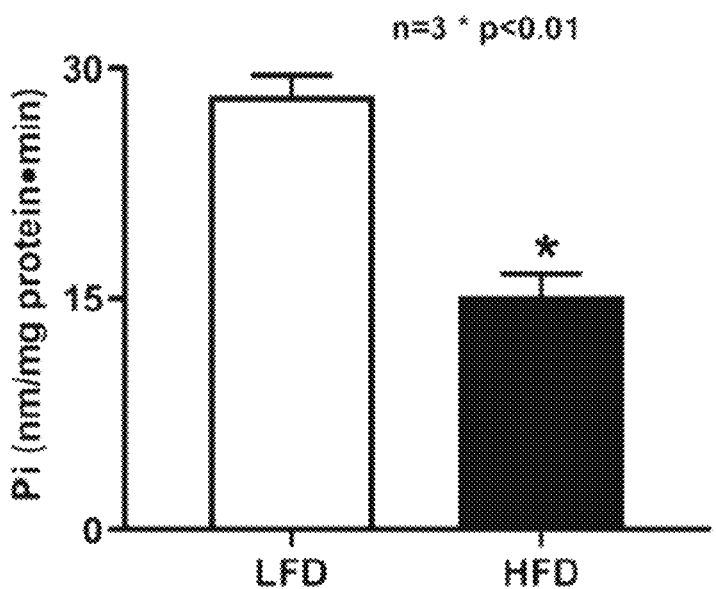
FIG. 9 is a graph showing that Na/K-ATPase activity was significantly decreased in villus cell homogenates from HFD compared to LFD fed mice.
Figure 10:
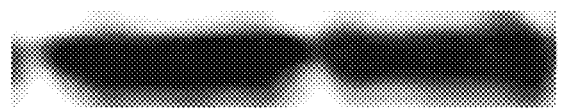
FIG. 10 is an image showing whole cell lysate villus cell SGLT1 protein expression was unchanged between LFD and HFD fed mice.

Example 2—Diet Induced Obesity in Mice and Rats Shows Increased Glucose and NaCl Absorption Similar to Genetic Models of Obesity in Tallyho Mouse and Zucker Rats and Humans To determine if glucose absorption (SGLT1) was stimulated in diet induced obesity in mice, C57BL/6 mice were fed with low fat diet (LFD) (10% calories from fat) and high fat diet (HFD)(60% calories from fat) from as soon as they are weaned until 21 weeks of age. Villus cells were then isolated and BBMV were prepared as described previously. $^3$H—OMG uptake was performed for SGLT1 activity. SGLT1 was significantly stimulated in HFD fed mice compared to LFD fed mice (FIG. 8). Since Na/K-ATPase provides the favorable transcellular Na gradient for SGLT1 in villus cells, Na/K-ATPase activity was determined by measuring the inorganic phosphate release assay in villus cell homogenates. As shown in FIG. 9, Na/K-ATPase activity was significantly decreased, not increased, in villus cells from HFD. This indicated that SGLT1 stimulation was not secondary to the Na extruding capacity of villus cells during diet-induced obesity. To study the molecular mechanism of stimulation of SGLT1, Western blot studies were carried out in whole cell lysates which showed that SGLT1 protein expression was unchanged between LFD and HFD (FIG. 10). These data demonstrated that SGLT1 is stimulated in a diet induced model of obesity comparable to what was seen in the leptin knockout model of obesity in rats.

Figure 11:
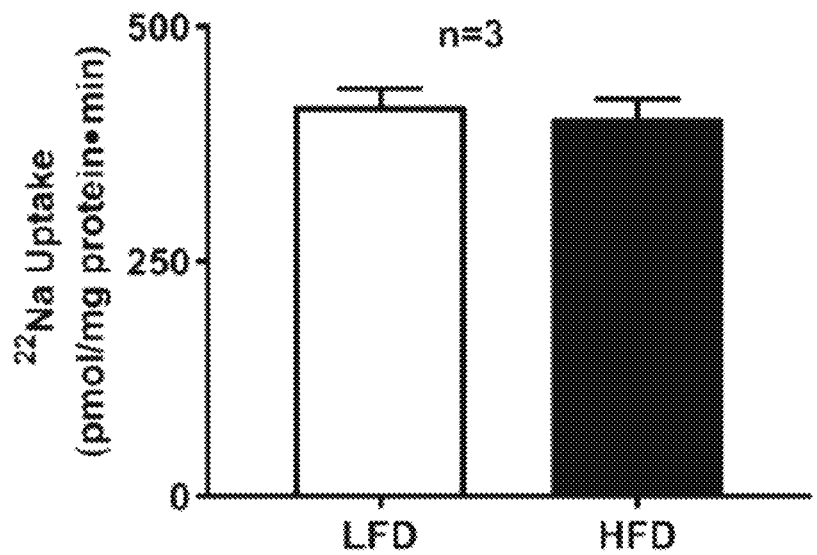
FIG. 11 is a graph showing Na/H exchange activity was unaffected in HFD fed mice compared to LFD.
Figure 12:
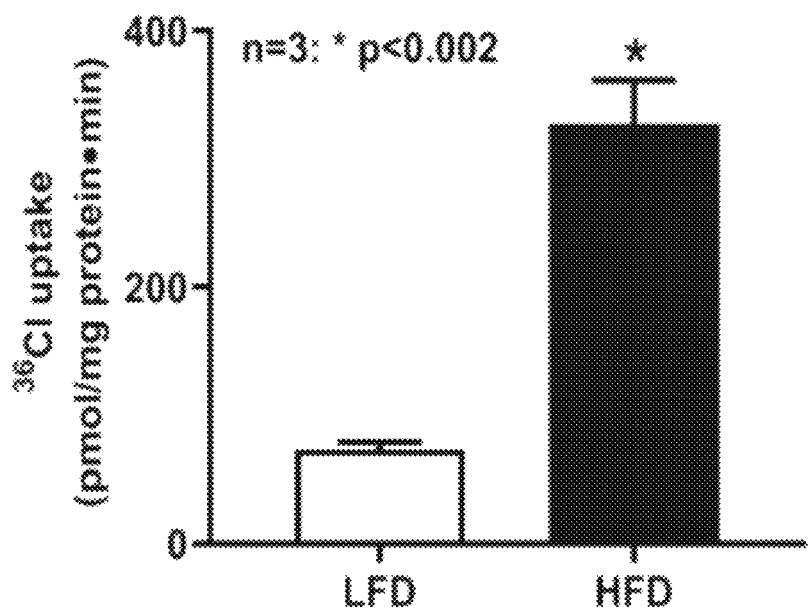
FIG. 12 is a graph showing Cl/HCO$_3$ uptake was significantly increased in villus cell BBM from HFD compared to LFD fed mice.
Figure 13:
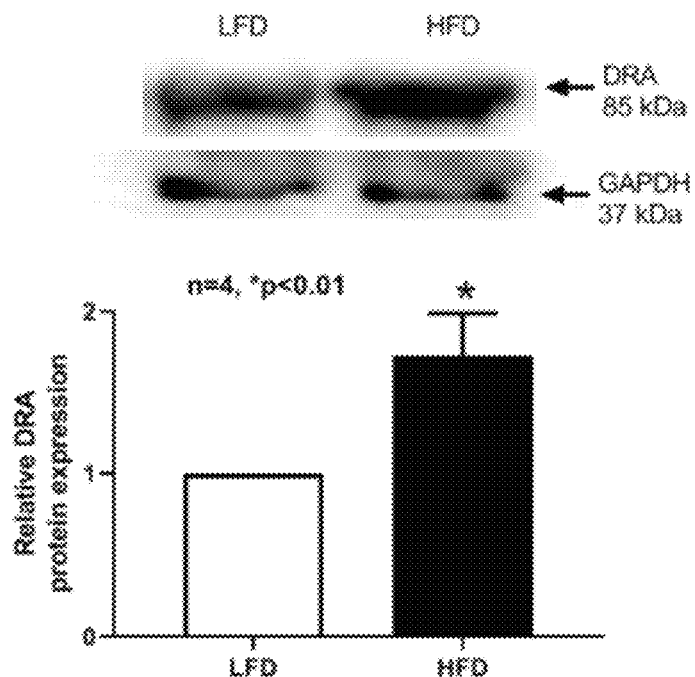
FIG. 13 is an image and graph showing whole cell lysate of villus cell DRA protein expression was significantly increased in HFD compared to LFD.
Figure 14:
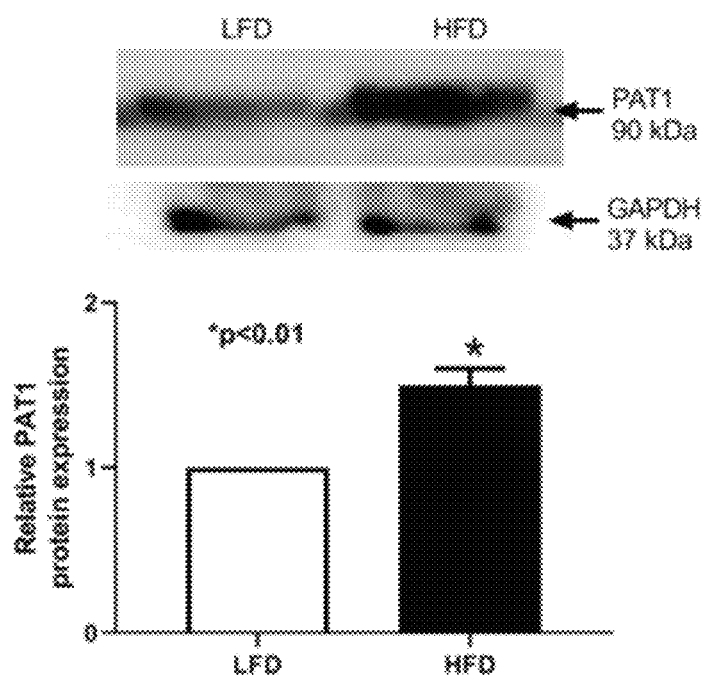
FIG. 14 is an image and graph showing PAT1 protein expression was significantly increased in HFD fed mice villus cells.

To determine if NaCl absorption was stimulated in diet induced obesity in mice, Na/H exchange activity was then examined. As shown in FIG. 11, Na/H exchange was unaffected between HFD and LFD fed mice, which led to the determination that Na/H exchange activity was not changed in diet-induced mouse model of obesity. Unlike Na/H exchange, however, Cl:$HCO_3$ exchange activity was increased in HFD compared to LFD (FIG. 12). To understand the molecular mechanism of Cl:$HCO_3$ exchange upregulation, Western blot studies were performed in villus cell whole cell lysate. Cl:$HCO_3$ is mediated by DRA and/or PAT-1 isoforms. DRA and PAT1 protein expressions were significantly increased in HFD compared to LFD fed mice (FIGS. 13-14, respectively). These data indicated that the mechanism of regulation of NaCl absorption during diet-induced obesity was novel, and secondary to the coupling of SGLT1 with DRA/PAT1 such that the insights from these studies could be used to derive better therapeutic options for the obesity mediated hypertension.

Figure 15:
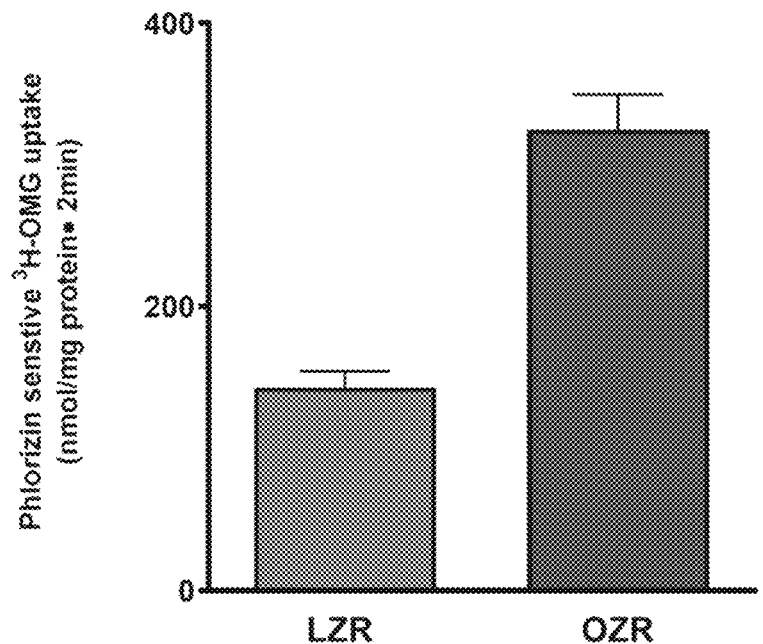
FIG. 15 is a graph showing SGLT1 activity was stimulated in OZR villus cells (n=4, *p<0.05).

Example 3—Adipose-Derived Secretome (ADS) Mediates the Stimulation of Intestinal Epithelial Cell Na-Glucose Co-Transport (SGLT1) During Obesity Obesity is a national epidemic and its most common complication is diabetes which results from altered glucose homeostasis. Glucose is the major source of energy for mammalian cells and is mainly absorbed by the sodium-dependent glucose co-transporter (SGLT1/SLC6A5) present on the brush border membrane (BBM) of intestinal villus cell. In obese Zucker rats, and as described above, SGLT1 was shown to be increased in villus cells (see also FIG. 15). In obesity, however, the adipose-derived secretome (ADS) has been shown to influence many physiological processes. Yet, whether the ADS may regulate SGLT1 during obesity was not known. In this regard, and without wishing to be bound by any particular theory or mechanism, it was believed that the ADS may uniquely regulate SGLT1 in intestinal epithelial cells during obesity, and experiments were thus undertaken to determine the mechanism of regulation of SGLT1 by the ADS in intestinal epithelial cells. Briefly, in these further experiments, non-transformed rat small intestinal epithelial cells (IEC-18) were grown on trans-wells. On day 4 post-confluence, IEC-18 cells were treated with ADS from lean (LZR) and obese (OZR) Zucker rats. Na-dependent $^3$H—OMG uptake studies were then performed for SGLT1 activity and Na-K-ATPase activity was measured as a function of inorganic phosphate release. Further, kinetic studies were conducted at varying extra vesicular OMG concentrations at 30 seconds and western blots were performed using a rat-specific SGLT1 antibody.

Figure 16:
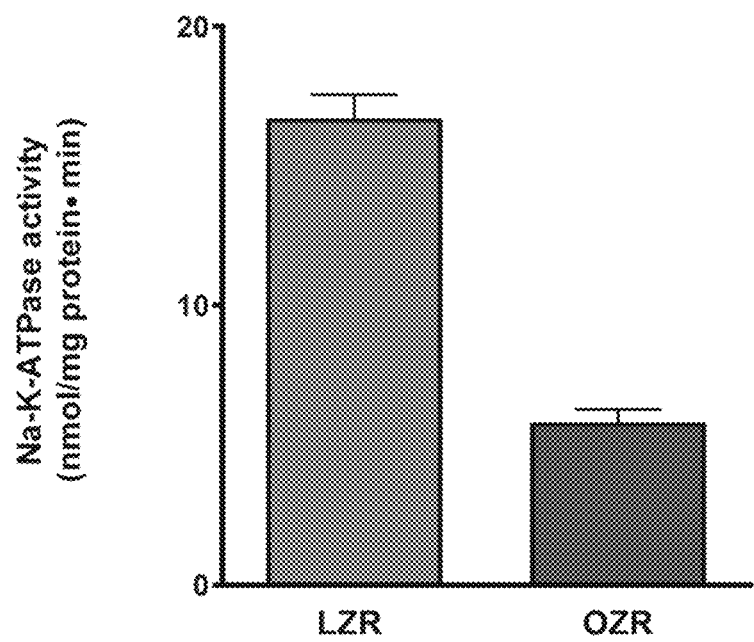
FIG. 16 is a graph showing Na-K-ATPase activity was inhibited in OZR villus cells (n=4, *p<0.05).
Figure 17:
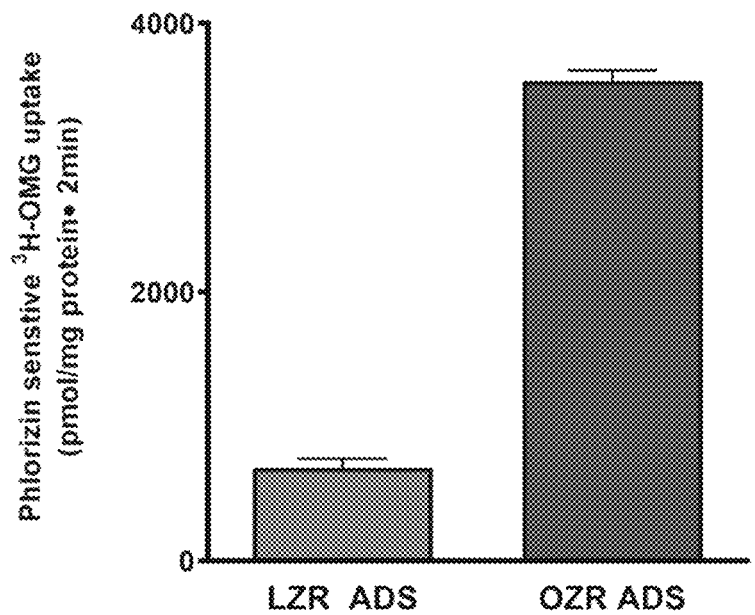
FIG. 17 is a graph showing that SGLT1 activity in IEC-18 cells was stimulated by OZR ADS (n=4, *p<0.05).
Figure 18:
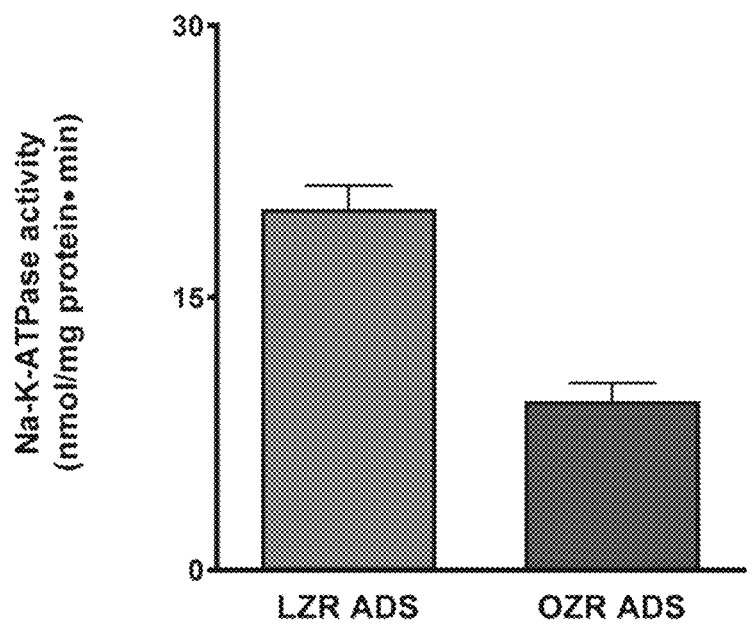
FIG. 18 is a graph showing Na-K-ATPase activity in IEC-18 cells, where Na-K-ATPase activity was inhibited by OZR ADS (n=4, *p<0.05).
Figure 19:
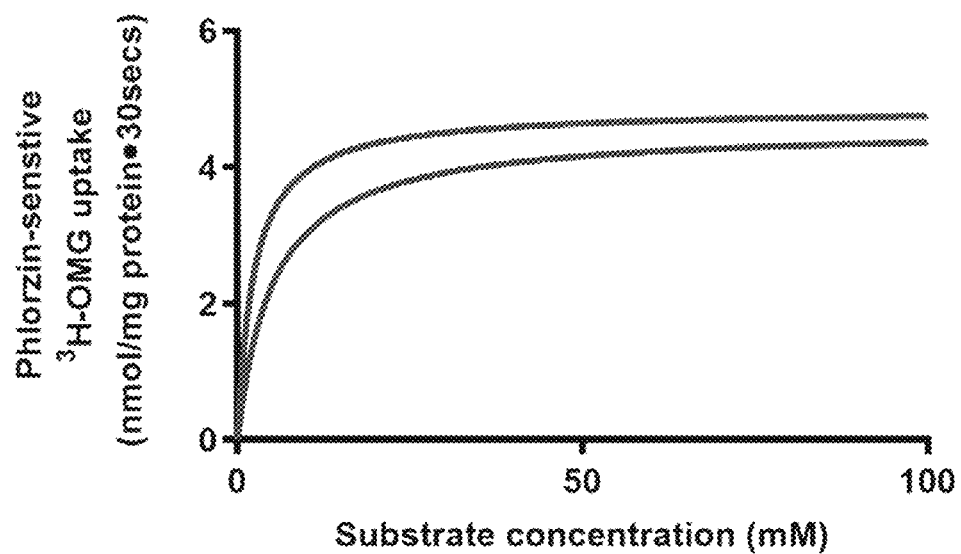
FIG. 19 includes a graph and associated table showing kinetic studies of Na-glucose co-transport in IEC-18 cells, where stimulation of SGLT1 by OZR ADS was secondary to an increase in the affinity ($11K_M$) of the co-transporter for glucose without a change in the maximal rate of uptake of glucose ($V_{max}$) (*p<0.01, n=3).
Figure 20:
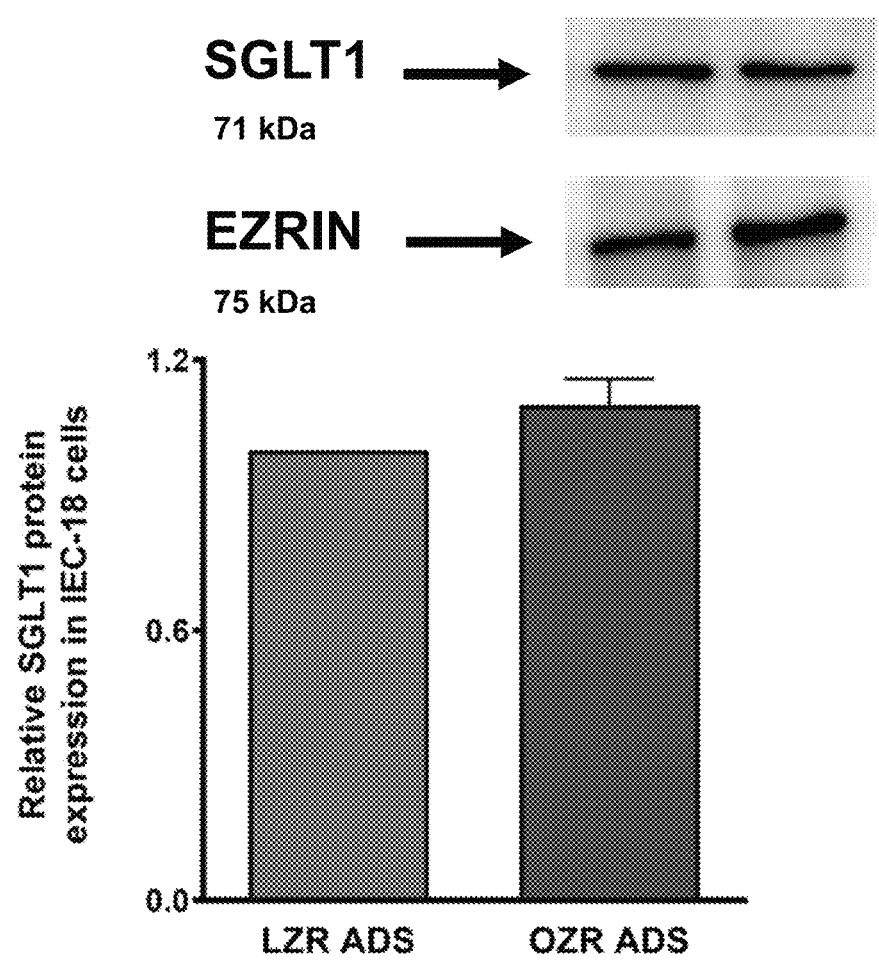
FIG. 20 is an image and graph showing SGLT1 protein expression in BBM of IEC-18 cells, where SGLT1 protein expression was unaltered by OZR ADS (n=3).

Upon the analysis of the results from these experiments, it was observed not only that in vivo OZR SGLT1 activity was increased in villus cells (FIG. 15), but that, in vitro, SGLT1 was stimulated by ADS from OZR in IEC-18 cells (FIG. 17). Additionally, both in vivo and in vitro OZR ADS inhibited the Na-K-ATPase (FIGS. 16 and 18), and thus, the stimulation of SGLT1 during obesity was not secondary to altered Na-extruding capacity of the cells. Kinetic studies (FIG. 19) also showed that the mechanism of stimulation of SGLT1 by OZR ADS was secondary to an increase in the affinity of the co-transporter for glucose without a change in the number of co-transporters. In particular, Western blot analysis demonstrated that the mechanism of stimulation of SGLT1 by OZR ADS was not secondary to altered protein expression (FIG. 20).

In summary, it was found that obese adipose-derived secretome stimulates SGLT1 in intestinal epithelial cells. The mechanism of stimulation of SGLT1 by OZR ADS in IEC-18 cells in vitro is identical to that seen in vivo in villus cells from obese Zucker rats. Thus, stimulation of villus cell SGLT1 during obesity can be mediated by the obese adipose-derived secretome.

Example 4—L-NAME Reverses Increased Absorption of Glucose and NaCl in Obese Rats Materials and Methods Animal models and treatment. Zucker rats (Strain code: 185 (Obese), 186 (Lean); 18 wks) obtained from Charles River Laboratories International, Inc. were used as a genetic model of obesity, and C57BL/6 mice (B6) (The Jackson Laboratory) and Sprague Dawley rats (Strain code: 400; Charles River Laboratories International, Inc.) were used as a diet-induced model of obesity. B6 mice were fed with either a low-fat diet (LFD) (10% calories from fat; Cat. No: 58124, LabDiet, USA) or high-fat diet (HFD) (60% calories from fat; Cat. No: 58126, LabDiet, USA) starting at 4 weeks of age until they reached 20 weeks of age. Sprague Dawley rats were fed the above-mentioned diets from the age of 12 weeks for 6 weeks to induce obesity. To inhibit constitutive nitric oxide production in both mice and rats, the animals were first treated with either a 10 or 25 mg/kg per day dosage of used $N^G$-nitro-L-arginine methyl ester (L-NAME). Studies determined that 10 mg dose of L-NAME was the lowest dose to consistently affect transporter activities and was therefore used in all subsequent experiments. For the diet-induced mice obesity model, LFD and HFD fed B6 mice were treated with this dose from the age of 20 weeks, and Sprague Dawley rats were treated from the age of 17 wks for 1 week. All the experimental animals were handled and euthanized according to Marshall University IACUC regulations.

Na-K-ATPase measurement. Na-K-ATPase activity was measured as inorganic phosphate released from cellular homogenates using a previously described method. Enzyme specific activity was expressed as nanomoles of Pi liberated per milligram protein per minute.

Uptake studies in intact villus cells and BBMVs. Intestinal cell isolation and BBMVs from Zucker rats, B6 mice, and Sprague Dawley rats were done by $Mg^{++}$ precipitation and differential centrifugation as previously described. Na-glucose co-transport uptake studies in intact villus cells (Zucker rats alone) and BBMVs (Zucker rats, TallyHo and human villus cells) were performed by the rapid-filtration technique as previously described. In brief, for intact villus cell uptake, 10 μl of villus cells were suspended in Na-free buffer containing 130 mM trimethyl ammonium chloride (TMACl), 4.7 mM KCl, 1 mM MgSO4, 1.25 mM CaCl2), 20 mM HEPES (pH 7.4). The villus cells were then incubated in 90 μl of reaction medium that contained 130 mM NaCl, 4.7 mM KCl, 1 mM MgSO4, 1.25 mM CaCl2), 20 mM HEPES (pH 7.4 at room temperature), 10 μCi of 3H—O-methyl glucose (OMG) and 100 μM OMG in the presence or absence of 1 mM phlorizin. At 2 min, uptake was arrested by mixing with an ice-cold stop solution (Na-free buffer) containing 25 mM D-glucose. The mixture was filtered on 0.65 m Millipore (HAWP) filters and washed twice with 5 ml ice-cold stop solution. Filters with intact villus cells were dissolved in 5 ml scintillation fluid (Ecoscint, National Diagnostics), and radioactivity was determined in a Beckman 6500 Beta Scintillation Counter. For BBMV uptakes, the uptakes were performed as indicated for intact villus cells but were arrested at 60 sec for mice and 90 sec for rats. The reaction mixture was filtered on 0.45 m Millipore (HAWP) filters and processed as described above. The uptake experiment results were expressed as Na-glucose co-transport uptake in nanomoles per milligram protein at 60 sec for mice or 90 sec for rats. To determine the kinetic parameters of BBM Na-glucose cotransport, BBMV uptakes were performed with increasing concentrations of extravesicular OMG, and the numbers obtained with kinetics experiments were analyzed using GraphPad Prism 7 (San Diego, CA) to derive kinetic parameters.

Na/H exchange uptake was measured in BBMV by rapid filtration technique as previously described. Briefly, 5 μl of BBMV were suspended in a buffer containing 300 mM mannitol, 50 mM Tris-MES (pH 5.5) or 50 mM Tris-HEPES (pH 7.5), and incubated in 95 μl of reaction medium containing 300 mM mannitol, 50 mM Tris-HEPES (pH 7.5 at room temperature), 1 mM $^{22}$NaCl and with or without 1 mM amiloride. At 60 sec, uptake was arrested by mixing with ice-cold stop solution (300 mM mannitol, 50 mM Tris-HEPES (pH 7.5)) and processed as described for Na-glucose co-transport uptake studies. The results were expressed as Na/H exchange in picomoles per milligram protein at 60 sec.

Cl/HCO$_3$ exchange uptake was measured in BBMV by rapid filtration technique as previously described. BBMV in vesicle medium containing 105 mM N-methyl-D-glucamine (NMG) gluconate, 50 mM HEPES-Tris pH 7.5 and either 50 mM KHCO$_3$ (vesicle gassed with 5% CO$_2$-95% N$_2$) or 50 mM potassium gluconate (vesicle gassed with 100% N$_2$). The reaction was started by adding 5 μl of the vesicle to 95 μl reaction mix containing 5 mM NMG-36Cl, 150 mM potassium gluconate, 50 mM MES-Tris pH 5.5, with or without 1 mM 4,4-Diisothiocyanatostilbene-2,2-disulfonic acid disodium salt (DIDS), a potent anion exchange inhibitor. The uptake was stopped at the desired time with an ice-cold stop solution containing 50 mM HEPES-Tris buffer (pH 7.5), 0.10 mM MgSO4, 50 mM potassium gluconate and 100 mM NMG gluconate and processed as described above. Results were calculated as the HCO$_3$ dependent DIDS sensitive Cl uptake.

Western Blot study. All the Western Blot experiments were performed with standard protocols and techniques with antibodies clearly validated through previous experiments. Solubilized BBM proteins from mice and rats were separated (custom made 8% polyacrylamide gel) and transferred to BioTrace PVDF membrane. For immunoreactive protein determination, membranes were probed with protein and species-specific antibodies. For mice, the anti-SGLT1 antibody raised in rabbit (ab14686, Abcam, USA) was used. For rat samples, an anti-SGLT1 antibody raised in chicken (Invitrogen custom antibody services, USA) was used. For NHE3, anti-NHE3 antibody raised in chicken (Invitrogen custom antibody services, USA) was used. Anti-DRA antibody raised in goat (sc-34939, Santa Cruz, USA), anti-PAT-1 antibody raised in goat (sc-26728, Santa Cruz, USA) were used for this study. For Western blot studies, horseradish peroxidase coupled specific secondary antibodies were used to detect the proteins before chemiluminescence with ECL Detection Reagent (GE Healthcare). The protein density of the specific proteins was quantitated with a densitometric scanner FluorChem™ instrument (Alpha Innotech, San Leandro, CA).

Protein assay. Proteins were quantified with the DCTM protein assay kit (Lowry's method) according to the manufacturer's protocols (Bio-Rad).

Results

Figure 21:
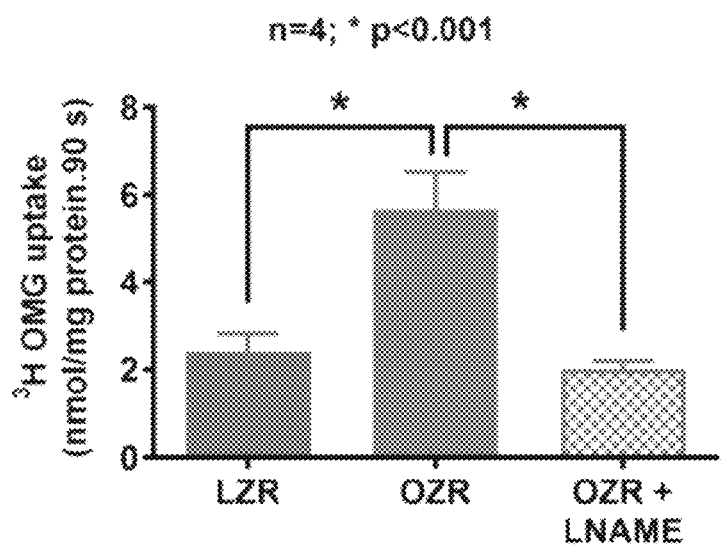
FIG. 21 is a graph showing administration of L-NAME reversed the stimulation of SGLT1 in obese rats.
Figure 22:
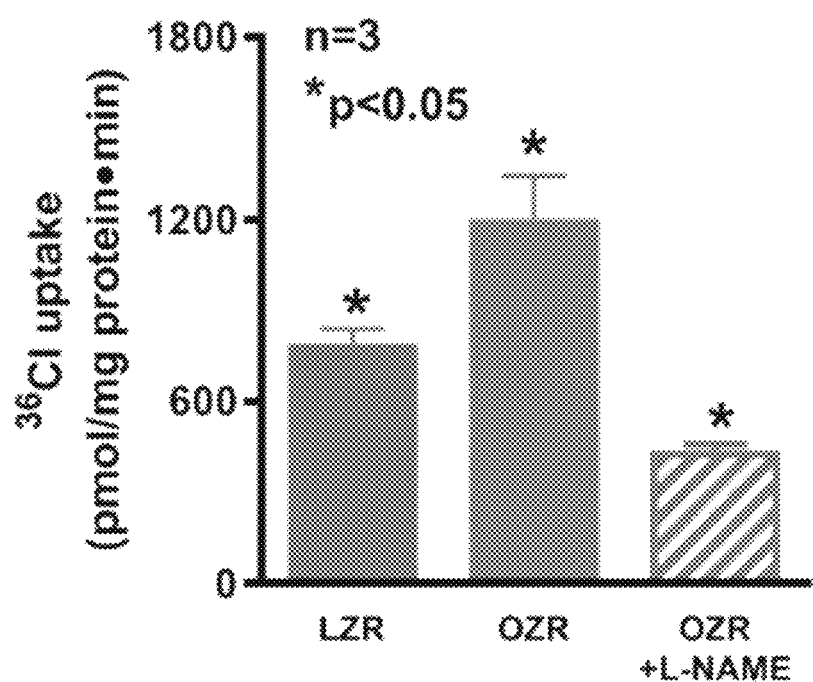
FIG. 22 is a graph showing administration of L-NAME reversed the stimulation of Cl:$HCO_3$ in obese rats.
Figure 23:
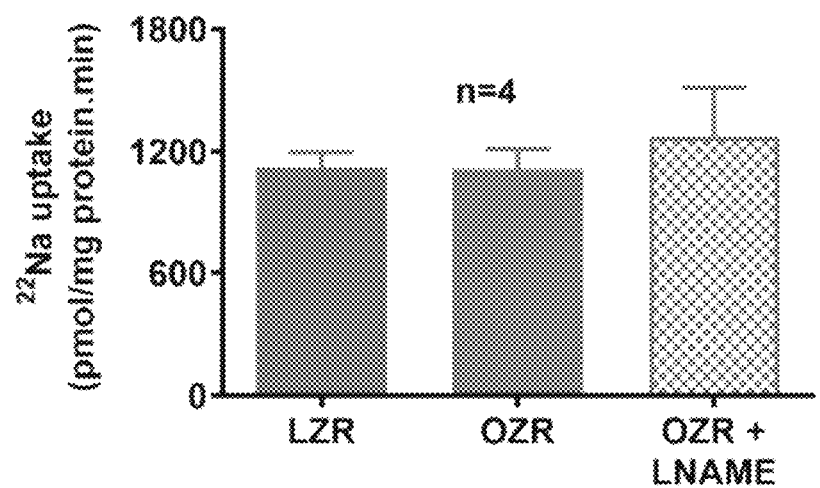
FIG. 23 is a graph showing administration of L-NAME does not affect NHE3 activity in obese rats.

Upon the analysis of the results from these experiments, it was observed that L-NAME reversed the stimulation of SGLT1 in obese rats. In particular, it was observed that glucose absorption was increased in obese rats (OZR), and that the increase was reversed when rats were treated for at least one week with L-NAME (FIG. 21). L-NAME also reversed the stimulation of Cl:HCO$_3$ in the obese rats. NaCl absorption was increased in obese rats (OZR), but that increase was reversed when rats were treated for at least one week with L-NAME (FIG. 22). It was further observed that L-NAME did not affect NHE3 in Obese Rats (FIG. 23)

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Saydah, S., Bullard, K. M., Cheng, Y., Ali, M. K., Gregg, E. W., Geiss, L., and Imperatore, G. (2014) Trends in cardiovascular disease risk factors by obesity level in adults in the United States, NHANES 1999-2010. Obesity (Silver Spring) 22, 1888-1895.
2. Centers for Disease Control and Prevention. (2017) National Diabetes Statistics Report, US Department of Health and Human Services, Atlanta, GA.
3. Centers for Disease Control and Prevention. (2016) High Blood Pressure Fact Sheet, High Blood Pressure in the United States. U.S. Department of Health and Human Services, Atlanta, GA, USA.
4. Lang, F., Bohmer, C., Palmada, M., Seebohm, G., Strutz-Seebohm, N., and Vallon, V. (2006) (Patho)physiological significance of the serum and glucocorticoid-inducible kinase isoforms. Physiol. Rev. 86, 1151-1178.
5. Sanchez-Aguayo, I., Torreblanca, J., Angeles de la Hermosa, M., Mate, A., Planas, J. M., and Vazquez, C. M. (2001) Morphological and functional abnormalities in the ileum of rats with spontaneous hypertension: studies on SGLT1 protein. Scand. J. Gastroenterol. 36, 494-501.
6. He, P., Zhao, L., Zhu, L., Weinman, E. J., De Giorgio, R., Koval, M., Srinivasan, S., and Yun, C. C. (2015) Restoration of Na+/H+ exchanger NHE3-containing macrocomplexes ameliorates diabetes associated fluid loss. J. Clin. Invest. 125, 3519-3531.
7. Leung, L., Kang, J., Rayyan, E., Bhakta, A., Barrett, B., Larsen, D., Jelinek, R., Willey, J., Cochran, S., Broderick, T. L., and Al-Nakkash, L. (2014) Decreased basal chloride secretion and altered cystic fibrosis transmembrane conductance regulatory protein, Villin, GLUT5 protein expression in jejunum from leptin-deficient mice. Diabetes Metab. Syndr. Obes. 7, 321-330.
8. Donowitz, M., Cha, B., Zachos, N. C., Brett, C. L., Sharma, A., Tse, C. M., and Li, X. (2005) NHERF family and NHE3 regulation. J. Physiol. 567, 3-11.
9. Sundaram, U., Knickelbein, R. G., and Dobbins, J. W. (1991) pH regulation in ileum: Na(+)-H+ and Cl(−)-HCO3− exchange in isolated crypt and villus cells. Am. J. Physiol. 260, G440-G449.
10. Zachos, N.C., Tse, M., and Donowitz, M. (2005) Molecular physiology of intestinal Na+/H+ exchange. Annu. Rev. Physiol. 67, 411-443
11. Donowitz, M., Mohan, S., Zhu, C. X., Chen, T. E., Lin, R., Cha, B., Zachos, N. C., Murtazina, R., Sarker, R., and Li, X. (2009) NHE3 regulatory complexes. J. Exp. Biol. 212, 1638-1646.
12. Kiela, P. R., Xu, H., and Ghishan, F. K. (2006) Apical NA+/H+ exchangers in the mammalian gastrointestinal tract. J. Physiol. Pharmacol. 57 (Suppl 7), 51-79.
13. Kato, A., and Romero, M. F. (2011) Regulation of electroneutral NaCl absorption by the small intestine. Annu. Rev. Physiol. 73, 261-281.
14. Malakooti, J., Saksena, S., Gill, R. K., and Dudeja, P. K. (2011) Transcriptional regulation of the intestinal luminal Na+ and Cl2 transporters. Biochem. J. 435, 313-325.
15. Mount, D. B., and Romero, M. F. (2004) The SLC26 gene family of multifunctional anion exchangers. Pflugers Arch. 447, 710-721.
16. Schultheis, P. J., Clarke, L. L., Meneton, P., Miller, M. L., Soleimani, M., Gawenis, L. R., Riddle, T. M., Duffy, J. J., Doetschman, T., Wang, T., Giebisch, G., Aronson, P. S., Lorenz, J. N., and Shull, G. E. (1998) Renal and intestinal absorptive defects in mice lacking the NHE3 Na+/H+ exchanger. Nat. Genet. 19, 282-285.
17. Alrefai, W. A., Tyagi, S., Gill, R., Saksena, S., Hadjiagapiou, C., butyrate uptake in Caco-2 cells by phorbol 12-myristate 13-acetate. Am. J. Physiol. Gastrointest. Liver Physiol. 286, G197-G203.
18. Yun, C. C., Chen, Y., and Lang, F. (2002) Glucocorticoid activation of Na(+)/H(+) exchanger isoform 3 revisited. The roles of SGK1 and NHERF2. J. Biol. Chem. 277, 7676-7683.
19. Amin, M. R., Dudeja, P. K., Ramaswamy, K., and Malakooti, J. (2007) Involvement of Sp1 and Sp3 in 19. differential regulation of human NHE3 promoter activity by sodium butyrate and IFN-gamma/TNFalpha. Am. J. Physiol. Gastrointest. Liver Physiol. 293, G374-G382.
20. Lenzen, H., Lunnemann, M., Bleich, A., Manns, M. P., Seidler, U., and J'orns, A. (2012) Downregulation of the NHE3-binding PDZ-adaptor protein PDZK1 expression during cytokine-induced inflammation in interleukin-10-deficient mice. PLoS One 7, e40657.
21. Palaniappan, B., and Sundaram, U. (2018) Direct and specific inhibition of constitutive nitric oxide synthase uniquely regulates brush border membrane Na-absorptive pathways in intestinal epithelial cells. Nitric Oxide 79, 8-13.
22. Coon, S., Kekuda, R., Saha, P., Talukder, J. R., and Sundaram, U. (2008) Constitutive nitric oxide differentially regulates Na-Hand Naglucose cotransport in intestinal epithelial cells. Am. J. Physiol. Gastrointest. Liver Physiol. 294, G1369-G1375.
23. Schweinfest, C. W., Spyropoulos, D. D., Henderson, K. W., Kim, J. H., Chapman, J. M., Barone, S., Worrell, R. T., Wang, Z., and Soleimani, M. (2006) slc26a3 (dra)-deficient mice display chloride-losing diarrhea, enhanced colonic proliferation, and distinct up-regulation of ion transporters in the colon. J. Biol. Chem. 281, 37962-37971.
24. Wang, Z., Wang, T., Petrovic, S., Tuo, B., Riederer, B., Barone, S., Lorenz, J. N., Seidler, U., Aronson, P. S., and Soleimani, M. (2005) Renal and intestinal transport defects in Slc26a6-null mice. Am. J. Physiol. Cell Physiol. 288, C957-C965.
25. Robinson, J. D., and Flashner, M. S. (1979) The (Na++K+)-activated ATPase.
Enzymatic and transport properties. Biochim. Biophys. Acta 549, 145-176.
26. Wright, E. M., Hirayama, B. A., and Loo, D. F. (2007) Active sugar transport in health and disease. J. Intern. Med. 261, 32-43.
27. Wright, E., Loo, D., Hirayama, B., and Turk, E. (2006) Sugar absorption. In: Physiology of Gastrointestinal Tract, 4th Ed. (Johnson, L., Barrett, K. E., Ghishan, F., Merchant, J., Said, H., and Wood, J., eds.), pp. 1653-1666, Elsevier/Academic Press, San Diego, CA, USA.
28. Poulsen, S. B., Fenton, R. A., and Rieg, T. (2015) Sodium-glucose cotransport. Curr. Opin. Nephrol. Hypertens. 24, 463-469.
29. Bickel, C. A., Knepper, M. A., Verbalis, J. G., and Ecelbarger, C. A. (2002) Dysregulation of renal salt and water transport proteins in diabetic Zucker rats. Kidney Int. 61, 2099-2110.
30. Kurtz, T. W., Morris, R. C., and Pershadsingh, H. A. (1989) The Zucker fatty rat as a genetic model of obesity and hypertension. Hypertension 13, 896-901.
31. Bray, G. A. (1977) The Zucker-fatty rat: a review. Fed. Proc. 36, 148-153.
32. Kim, J. H., and Saxton, A. M. (2012) The TALLYHO mouse as a model of human type 2 diabetes. Methods Mol. Biol. 933, 75-87.
33. Joost, H. G., and Schurmann, A. (2014) The genetic basis of obesity associated type 2 diabetes (diabesity) in polygenic mouse models. Mamm. Genome 25, 401-412.
34. Mao, X., Dillon, K. D., McEntee, M. F., Saxton, A. M., and Kim, J. H. (2014) Islet insulin secretion, b-cell mass, and energy balance in a polygenic mouse model of type 2 diabetes with obesity. J. Inborn Errors Metab. Screen. 2, 1-6.
35. Sung, Y. Y., Lee, Y. S., Jung, W. H., Kim, H. Y., Cheon, H. G., Yang, S. D., and Rhee, S. D. (2005) Glucose intolerance in young TallyHo mice is induced by leptin-mediated inhibition of insulin secretion. Biochem. Biophys. Res. Commun. 338, 1779-1787.
36. Rhee, S. D., Sung, Y. Y., Lee, Y. S., Kim, J. Y., Jung, W. H., Kim, M. J., Lee, M. S., Lee, M. K., Yang, S. D., and Cheon, H. G. (2011) Obesity of TallyHO/JngJ mouse is due to increased food intake with early development of leptin resistance. Exp. Clin. Endocrinol. Diabetes 119, 243-251.
37. Parkman, J. K., Mao, X., Dillon, K., Gudivada, A., Moustaid-Moussa, N., Saxton, A. M., and Kim, J. H. (2016) Genotype-dependent metabolic responses to semi-purified high-sucrose high-fat diets in the TALLYHO/jng vs. C57bl/6 mouse during the development of obesity and type 2 diabetes. Exp. Clin. Endocrinol. Diabetes 124, 622-629.
38. Coon, S., Kekuda, R., Saha, P., and Sundaram, U. (2011) Reciprocal regulation of the primary sodium absorptive pathways in rat intestinal epithelial cells. Am. J. Physiol. Cell Physiol. 300, C496-C505.
39. Manoharan, P., Gayam, S., Arthur, S., Palaniappan, B., Singh, S., Dick, G. M., and Sundaram, U. (2015) Chronic and selective inhibition of basolateral membrane Na-K-ATPase uniquely regulates brush border membrane Na absorption in intestinal epithelial cells. Am. J. Physiol. Cell Physiol. 308, C650-C656.
40. Forbush, B., III (1983) Assay of Na,K-ATPase in plasma membrane preparations: increasing the permeability of membrane vesicles using sodium dodecyl sulfate buffered with bovine serum albumin. Anal. Biochem. 128, 159-163.
41. Sundaram, U., Coon, S., Wisel, S., and West, A. B. (1999) Corticosteroids reverse the inhibition of Na-glucose cotransport in the chronically inflamed rabbit ileum. Am. J. Physiol. 276, G211-G218.
42. Sundaram, U., Wisel, S., Rajendren, V. M., and West, A. B. (1997) Mechanism of inhibition of Na+-glucose cotransport in the chronically inflamed rabbit ileum. Am. J. Physiol. 273, G913-G919.
43. Sundaram, U., and West, A. B. (1997) Effect of chronic inflammation on electrolyte transport in rabbit ileal villus and crypt cells. Am. J. Physiol. 272, G732-G741.
44. Sundaram, U., Wisel, S., and Fromkes, J. J. (1998) Unique mechanism of inhibition of Na+-amino acid cotransport during chronic ileal inflammation. Am. J. Physiol. 275, G483-G489.
45. Turner, J. R., and Black, E. D. (2001) NHE3-dependent cytoplasmic alkalinization is triggered by Na(+)-glucose cotransport in intestinal epithelia. Am. J. Physiol. Cell Physiol. 281, C1533-C1541.
46. Coon, S., and Sundaram, U. (2003) Unique regulation of anion/HCO$_3$- exchangers by constitutive nitric oxide in rabbit small intestine. Am. J. Physiol. Gastrointest. Liver Physiol. 285, G1084-G1090.
47. Manokas, T., Fromkes, J. J., and Sundaram, U. (2000) Effect of chronic inflammation on ileal short-chain fatty acid/bicarbonate exchange. Am. J. Physiol. Gastrointest. Liver Physiol. 278, G585-G590.
48. Manoharan, P., Coon, S., Baseler, W., Sundaram, S., Kekuda, R., and Sundaram, U. (2013) Prostaglandins, not the leukotrienes, regulate Cl(−)/HCO(3)(−) exchange (DRA, SLC26A3) in villus cells in the chronically inflamed rabbit ileum. Biochim. Biophys. Acta 1828, 179-186.
49. Hodges, K., Gill, R., Ramaswamy, K., Dudeja, P. K., and Hecht, G. (2006) Rapid activation of Na+/H+ exchange by EPEC is PKC mediated. Am. J. Physiol. Gastrointest. Liver Physiol. 291, G959-G968.
50. Kumar, K. M., Aruldhas, M. M., Banu, S. L., Sadasivam, B., Vengatesh, G., Ganesh, K. M., Navaneethabalakrishnan, S., Navin, A. K., Michael, F. M., Venkatachalam, S., Stanley, J. A., Ramachandran, I., Banu, S. K., and Akbarsha, M. A. (2017) Male reproductive toxicity of CrVI: in utero exposure to CrVI at the critical window of testis differentiation represses the expression of Sertoli cell tight junction proteins and hormone receptors in adult F1 progeny rats. Reprod. Toxicol. 69, 84-98.
51. Gorboulev, V., Schurmann, A., Vallon, V., Kipp, H., Jaschke, A., Klessen, D., Friedrich, A., Scherneck, S., Rieg, T., Cunard, R., Veyhl-Wichmann, M., Srinivasan, A., Balen, D., Breljak, D., Rexhepaj, R., Parker, H. E., Gribble, F. M., Reimann, F., Lang, F., Wiese, S., Sabolic, I., Sendtner, M., and Koepsell, H. (2012) Na(+)-D-glucose cotransporter SGLT1 is pivotal for intestinal glucose absorption and glucose-dependent incretin secretion. Diabetes 61, 187-196.
52. Forbush B, 3rd (1983) Assay of Na,K-ATPase in plasma membrane preparations: increasing the permeability of membrane vesicles using sodium dodecyl sulfate buffered with bovine serum albumin. *Analytical biochemistry* 128 (1):159-163.
53. Sundaram U, Wisel S, Rajendren V, West A (1997) Mechanism of inhibition of Na+-glucose cotransport in the chronically inflamed rabbit ileum. *American Journal of Physiology-Gastrointestinal and Liver Physiology* 273 (4):G913-G919.
54. Sundaram U, Wisel S, Fromkes J (1998) Unique mechanism of inhibition of Na+-amino acid cotransport during chronic ileal inflammation. *American Journal of Physiology—Gastrointestinal and Liver Physiology* 275(3): G483-G489.
55. Turner J R, Black E D (2001) NHE3-dependent cytoplasmic alkalinization is triggered by Na+-glucose cotransport in intestinal epithelia. *American Journal of Physiology-Cell Physiology* 281(5):C1533-C1541.
56. Coon S, Sundaram U (2003) Unique regulation of anion/HCO3- exchangers by constitutive nitric oxide in rabbit small intestine. *American journal of physiology. Gastrointestinal and liver physiology* 285(6):G1084-1090.
57. Coon S, Kim J, Shao G, Sundaram U (2005) Na-glucose and Na-neutral amino acid cotransport are uniquely regulated by constitutive nitric oxide in rabbit small intestinal villus cells. *American Journal of Physiology-Gastrointestinal and Liver Physiology* 289(6):G1030-G1035.
58. Manokas T, Fromkes J J, Sundaram U (2000) Effect of chronic inflammation on ileal short-chain fatty acid/bicarbonate exchange. *American Journal of Physiology—Gastrointestinal and Liver Physiology* 278(4):G585-G590.
59. Manoharan P, et al. (2013) Prostaglandins, not the leukotrienes, regulate Cl(−)/HCO(3)(−) exchange (DRA, SLC26A3) in villus cells in the chronically inflamed rabbit ileum. *Biochimica et biophysica acta* 1828(2):179-186.
60. Palaniappan B, Arthur S, Sundaram V L, Butts M, Sundaram S, Mani K, Singh S, Nepal N, Sundaram U. (2019). Inhibition of intestinal villus cell Na/K-ATPase mediates altered glucose and NaCl absorption in obesity-associated diabetes and hypertension. The FASEB Journal, 33(8), 9323-9333.
61. Arthur S, Coon S, Kekuda R, Sundaram U (2014) Regulation of sodium glucose co-transporter SGLT1 through altered glycosylation in the intestinal epithelial cells. Biochimica et biophysica acta 1838(5):1208-1214.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating obesity, comprising:
identifying a subject as having obesity associated with diabetes and hypertension;
identifying the subject as having a deregulation of glucose and sodium chloride homeostasis; and
administering to the subject an effective amount of a therapeutic agent capable of reversing an inhibition of a Na/K-ATPase in a small intestine of the subject, wherein the therapeutic agent is NG-nitro-L-arginine methyl ester (L-NAME).

2. The method of claim 1, wherein the Na/K-ATPase is a basolateral membrane Na/K-ATPase.

3. The method of claim 1, wherein administering the therapeutic agent decreases an amount of glucose transport and/or decreases an amount of sodium chloride (NaCl) absorption in the small intestine of the subject.

4. The method of claim 3, wherein administering the therapeutic agent decreases glucose transport by a Na-glucose cotransport 1 (SGLT1) protein in the small intestine.

5. The method of claim 3, wherein administering the therapeutic agent decreases an activity or expression level of a down-regulated in adenoma (DRA) protein and/or putative anion transporter 1 (PAT1) protein in the small intestine.

6. The method of claim 2, wherein administering the therapeutic agent comprises contacting a villus cell in the small intestine of the subject with the therapeutic agent.

* * * * *